United States Patent [19]

Partridge et al.

[11] 4,421,690

[45] Dec. 20, 1983

[54] PROCESS FOR THE PREPARATION OF 24,24-DIFLUORO-1α,25-DIHYDROXY VITAMIN D₃ AND INTERMEDIATES OBTAINED THEREFROM

[75] Inventors: John J. Partridge, Upper Montclair; Shian-Jan Shiuey, Nutley; Milan R. Uskokovic, Upper Montclair, all of N.J.

[73] Assignee: Hoffmann-La Roche Inc., Nutley, N.J.

[21] Appl. No.: 379,387

[22] Filed: May 17, 1982

[51] Int. Cl.³ .............................................. C07J 9/00
[52] U.S. Cl. .............................. 260/397.1; 260/397.2; 260/397.4
[58] Field of Search ........................... 260/397.1, 397.2

[56] References Cited

U.S. PATENT DOCUMENTS 4,284,577  8/1981  Yamada et al. .................. 260/397.2

*Primary Examiner*—Elbert L. Roberts
*Attorney, Agent, or Firm*—Jon S. Saxe; Bernard S. Leon; William G. Isgro

[57] ABSTRACT

The present invention relates to a process and intermediates for the preparation of 24,24-difluoro-1α,25-dihydroxycholecalciferol from the readily-available 1α,3β-dihydroxyandrost-5-en-17-one which is made by a known microbiological process from 3β-hydroxyandrost-5-en-17-one [R. M. Dodson, A. H. Goldkamp and R. D. Muir, J. Amer. Chem. Soc. 82 4026 (1960)].

47 Claims, No Drawings

PROCESS FOR THE PREPARATION OF 24,24-DIFLUORO-1α,25-DIHYDROXY VITAMIN D₃ AND INTERMEDIATES OBTAINED THEREFROM

BACKGROUND OF THE INVENTION

This invention relates to a process for the preparation of 24,24-difluoro-1α,25-dihydroxycholecalciferol.

Vitamin D₃ or cholecalciferol is a well-known agent for the control of calcium and phosphorous homeostasis. In the normal animal or human, this compound is known to stimulate intestinal calcium transport and bone-calcium mobilization and is effective in preventing rickets.

It is also now well known that to be effective, vitamin D₃ must be converted in vivo to its hydroxylated forms. For example, the vitamin is first hydroxylated in the liver to form 25-hydroxy-vitamin D₃ and is further hydroxylated in the kidney to produce 1α,25-dihydroxy vitamin D₃ or 24R,25-dihydroxy vitamin D₃. The 1α,25-dihydroxylated form of the vitamin is generally considered to be the physiologically-active or hormonal form of the vitamin and to be responsible for what are termed the vitamin D-like activities such as increasing intestinal absorption of calcium and phosphate and mobilizing bone mineral.

SUMMARY OF THE INVENTION

The present invention relates to a process for preparing 24,24-difluoro-1α,25-dihydroxycholecalciferol from the readily-available 1α,3β-dihydroxyandrost-5-en-17-one which is made by a known microbiological process from 3β-hydroxyandrost-5-en-17-one [R. M. Dodson, A. H. Goldkamp and R. D. Muir, *J. Amer. Chem. Soc.*, 82 4026(1960)], as well as intermediates.

The synthesis involves as key steps the introduction at the 20-position of the properly-substituted 6-carbon moiety by alkylation, that is, the 25-hydroxy-24,24-difluorinated side chain, the reduction sequence to form the desired 20R-methyl group, the formation of 24,24-difluorocholesta-5,7-dienes and the final photolysisthermolysis sequence affording 24,24-difluoro-1α,25-dihyroxycholecalciferol.

DETAILED DESCRIPTION OF THE INVENTION

As used throughout the specification and the appended claims, the term "lower alkyl" denotes a monovalent substituent consisting solely of carbon and hydrogen of from 1 to 8 carbon atoms which may be straight- or branched-chain. Examples of lower alkyl groups are methyl, ethyl, n-propyl, i-propyl, tert-butyl, hexyl, heptyl, octyl and the like. The term "lower alkylene" denotes a divalent substituent consisting solely of carbon and hydrogen of from 1 to 8 carbon atoms which may be straight- or branched chain and whose free valences are attached to two distinct groups. Examples of alkylene groups are methylene, ethylene, propylene, butylene, amylene, hexylene, heptylene, octylene and the like. The term "lower alkoxy" refers to a lower alkyl ether group. Examples of alkoxy groups are methoxy, ethoxy, isopropoxy, tert-butoxy and the like. The term "phenyl-lower alkoxy" refers to a lower alkoxy group which is substituted by a phenyl ring. Examples of phenyl-lower alkoxy groups are benzyloxy, 2-phenylethoxy, 4-phenylbutoxy and the like. The term "alkanoyloxy group" refers to the residue of an aliphatic carobxylic acid of from 1 to 8 carbon atoms formed by removal of the hydrogen from the hydroxyl portion of the carboxyl group. Examples of alkanoyloxy groups are formyloxy, acetoxy, butyroyloxy, hexanoyloxy and the like. The term "substituted" as applied to "phenyl" refers to phenyl which is substituted with one or more of the following groups: alkyl, halogen (that is, fluorine, chlorine, bromine or iodine), nitro, cyano, trifluoromethyl and the like. The term aralkyl denotes a radical in which a lower alkyl H atom is substituted by an aryl group. Exemplary of aralkyl are benzyl, phenylethyl, phenylpropyl and the like. The term aryl denotes an organic radical derived from an aromatic hydrocarbon by the removal of a hydrogen atom. Exemplary of aryl are phenyl and substituted phenyl. The term alkanoyl denotes the residue of an aliphatic carboxylic acid of from 1 to 8 carbon atoms formed by the removal of hydroxyl from the carboxyl group. Exemplary of alkanoyl are acetyl, propionyl, butyroyl, pentanoyl and the like. The term aralkanoyl denotes an alkanoyl radical in which one hydrogen of the alkyl portion of the molecule has been substitued by aryl. Exemplary of aralkanoyl are phenylacetyl, phenylpropionyl, phenylbutyroyl, phenylpentanoyl and the like. The term aroyl denotes the residue of an aromatic carboxyl acid of from 7 to 20 carbon atoms formed by the removal of a hydroxy group from the carboxyl group. Exemplary of aroyl are benzoyl, toloyl and the like. The term acyl denotes the residue of an aliphatic or aromatic carboxylic acid formed by the removal of the hydroxyl portion of the carboxyl group. Exemplary of acyl are aroyl and alkaoyl.

In the steroid formulas presented herein, the various asymmetric substituents are illustrated as joined to the steroid nucleus by one of these notations: a solid line (—◀) indicating a substituent which is in the β-orientation, that is, above the plane of the molecule, a dotted line (---) indicating a substituent which is in the α-orientation, that is, below the plane of the molecule or a wavy line ( ∽ ) indicating a substituent which may be in the α- or β-orientation. The formulas have all been drawn to show the compounds in their absolute stereochemical configurations. Since the starting materials are derived from a naturally-occurring steroid (3β-hydroxyandrost-5-en-17-one) the products exist in the single absolute configuration depicted herein. However, the processes of the present invention are intended to apply as well to the synthesis of steroids of the "unnatural enantiomer" and racemic series, that is, the epimers of the compounds depicted herein and mixtures of both. Thus, one may begin the synthesis utilizing "unnatural" or racemic starting materials to prepare either "unnatural" or racemic products, respectively.

The Greek letter xi (ξ) in the name of a vitamin D₃ intermediate or metabolite indicates that the stereochemistry of the substituent to which it refers is undefined or that the product consists of a mixture of compounds epimeric at the designated position.

The nomenclature adopted to define absolute configuration of substituents bound to carbon atom 20 of the steroid nucleus is described in the Journal of Organic Chemistry, 34 (1970) 2849 under the title "IUPAC Tentative Rules for the Nomenclature of Organic Chemistry. Section E. Fundamental Stereochemistry".

In the process of the present invention, 24,24-difluoro-1α,25-dihydroxycholecalciferol of the formula

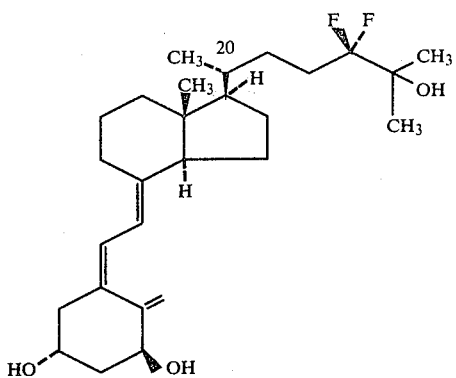

wherein F is fluorine,
is prepared by treating a compound of the formula

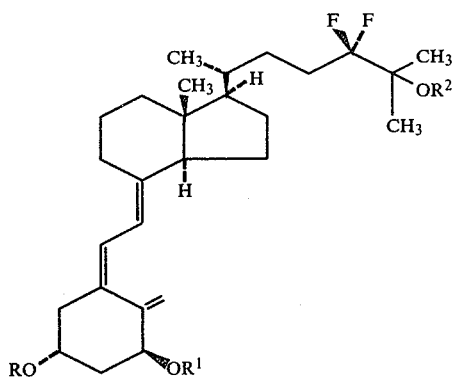

wherein F is fluorine and R, $R^1$, and $R^2$, independently, are lower alkyl, aralkyl, aryl, tri-lower alkylsilyl, di-lower alkylarylsilyl, lower-alkyldiarylsilyl, triarylsilyl or a group of the formula

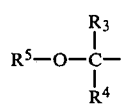

wherein $R^3$ is hydrogen or lower alkyl; $R^4$ and $R^5$ each independently are lower alkyl and $R^4$ and $R^5$ taken together are lower alkylene of from 3 to 6 carbon atoms
with an acid or tri-lower alkylsilyl iodide, or is prepared by treating a compound of the formula

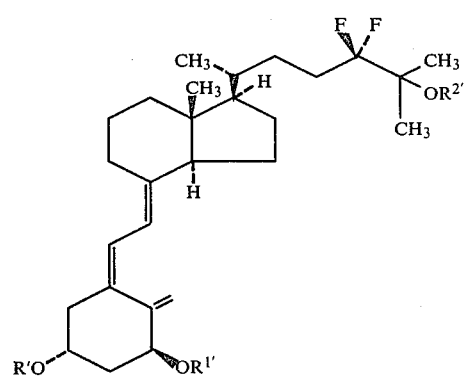

wherein F is as above and R', $R^{1'}$ and $R^{2'}$ are independently, hydrogen, lower alkanoyl, aralkanoyl or aroyl,
with a saponifying agent.

Within the scope of the invention are substituted cholesterol derivatives of the formula

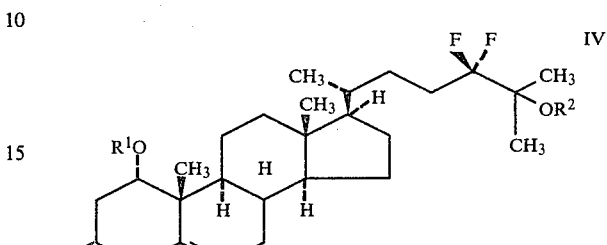

wherein $F, R, R^1$, and $R^2$ are as above,
and substituted cholesterol derivatives of the formula

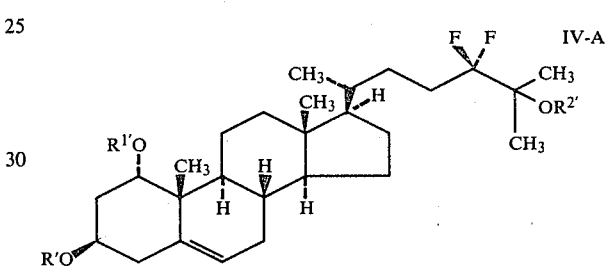

wherein $F, R', R^{1'}$, and $R^{2'}$ are as above,
which are useful as intermediates in the process of the invention.

The starting materials for the process of the invention are pregn-5-en-21-oic acid esters of the formula

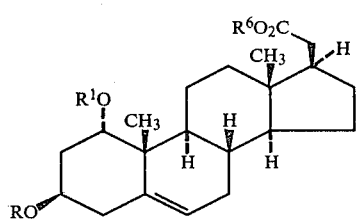

wherein R and $R^1$ are as above and $R^6$ is lower alkyl, aralkyl, or aryl.

The compounds of formula V can be prepared according to the following methodology starting with the known [1α,3β]-dihydroxyandrost-5-en-17-one (Formula V-A) [R. M. Dodson, A. H. Goldkamp and R. D. Muir, J. Amer. Chem. Soc., 82 4026(1960)]. The sequence (formula V-A→formula V) parallels the work of J. Wicha and K. Bal, J. Chem. Soc., Perkin Trans I (1978) 1282.

An intermediate of formula V, which is utilized hereinafter, can be prepared as follows:

Scheme I

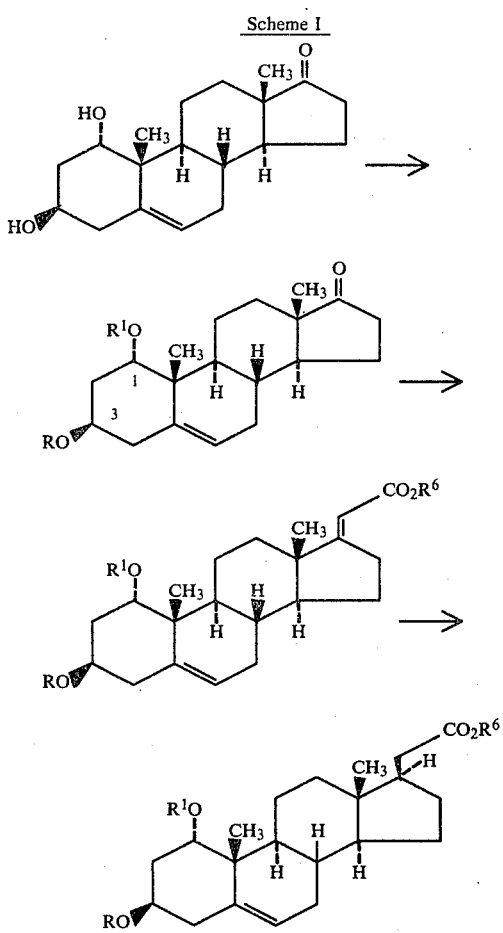

wherein R, R$^1$ and R$^6$ are as above.

The hydroxy groups in [1α,3β]-1,3-dihydroxyandrost-5-ene-17-one (formula V-A) were protected as acetals, ethers, or silyl ethers to yield compounds of of formula V-B, as described below.

To form acetal protecting groups the compound of formula V-A was treated with lower alkyl or aromatic vinyl ethers and a catalytic amount of a strong acid such as p-toluenesulfonic acid or hydrochloric acid in an inert solvent such as the ethers, diethyl ether or tetrahydrofuran or inert organic solvents such as benzene, toluene, or methylene chloride at a temperature range of −50° C. to 50° C., most preferably −50° C. to 0° C. to yield acetal compounds of formula V-B.

Exemplary of lower alkyl vinyl ethers are methyl vinyl ether, ethyl vinyl ether, methyl 1-methylvinyl ether, methyl 2-methylvinyl ether and the like. Exemplary of aromatic ethers are phenyl vinyl ether, phenyl 1-methyl-vinyl ether, phenyl 2-methyl vinyl ether and the like. The aforementioned aromatic ethers may be substituted, and are exemplified by 4-methylphenyl vinyl ether, 4-chlorophenyl vinyl ether, 4-methylphenyl 1-methylvinyl ether and the like. The aforementioned lower alkyl vinyl ethers may include cyclic vinyl ethers (3,4-dihydro-2H-pyrans and 2,3-dihydro-2H-furans).

To form ether protecting groups the compound of formula V-A was treated with lower alkyl, aralkyl or aryl halide and a tertiary amine or aromatic tertiary amine base in an inert solvent such as benzene, toluene or methylene chloride, an ether solvent such as diethyl ether or tetrahydrofuran or a tertiary amine solvent such as triethylamine or pyridine. Suitable tertiary amine or aromatic tertiary amine bases include triethyl amine, pyridine, s-collidine and 4-dimethylaminopyridine. Suitable lower alkyl halides include methyl iodide, ethyl iodide and the like. Suitable aralkyl halides include benzyl chloride, p-methoxybenzyl chloride, p-nitrobenzyl bromide and the like. Suitable aryl halides include iodobenzene, p-nitrophenyl iodide and the like. The reactions are typically carried out at a temperature range of −20° C. to 100° C. to yield ether compounds of formula V-B.

To form silyl ether protecting groups the compound of formula V-A was treated with tri-lower alkylsilyl halides such as trimethylsilyl chloride, trimethylsilyl bromide, and t-butyl dimethylsilyl chloride, di-lower alkylarylsilyl halides, such as dimethylphenylsilyl chloride, lower alkyldiarylsilyl halides such as methyldiphenylsilyl chloride, and triarylsilyl halides such as triphenylsilyl iodide and a tertiary amine base such as triethylamine or imidazole or an aromatic tertiary amine base such as pyridine or 4-dimethylaminopyridine. Suitable solvents include polar aprotic solvents such as dimethylformamide, inert solvents such as benzene, toluene, and methylene chloride, and ether solvents such as diethyl ether and tetrahydrofuran. Suitable temperatures include −20° C. to 100° C., most preferably 0° C. to 50° C. to yield silyl ether compounds of formula V-B.

The compounds of formula V-B were treated with a Horner-Wittig reagent and a base to yield compounds of the formula V-C. Suitable Horner-Wittig reagents include lower alkylphosphonoacetates such as triethylphosphonoacetate, aralkyl phosphonoacetates such as benzyl diethylphosphonoacetate and arylphophosphonoacetates such as phenyl diethylphosphonoacetate and triphenylphosphonoacetate. Suitable bases and solvents include alkali metal alkoxides such as sodium ethoxide in ethanol, potassium methoxide in methanol and the like and alkali metal hydrides such as sodium hydride and potassium hydride in inert solvents such as the ethers, diethyl ether, tetrahydrofuran and the like or polar aprotic solvents such as dimethyl sulfoxide and hexamethylphosphoramide. Suitable temperatures are in the range of from −20° C. to 120° C., most preferably at 20° C. to 80° C.

A compound of formula V-C is converted to a compound of formula V by catalytic hydrogenation over a noble metal catalyst. Suitable noble metal catalysts include platinum oxide, platinum metal, platinum on charcoal, palladium metal, and palladium on charcoal. Suitable solvents include lower alkanols of 1 to 8 carbon atoms such as methanol and ethanol, aliphatic carboxylic acid esters such as ethyl acetate, inert solvents such as methylene chloride, and ether solvents such as tetrahydrofuran, diethyl ether, p-dioxane and the like. The reactions are typically run under 1 atmosphere of hydrogen at temperatures of 0° C. to 50° C., most preferably at 0°–30° C.

In the process of the invention, a pregn-5-en-21-oic acid ester of the formula

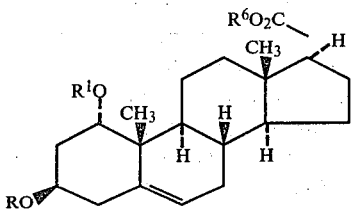

V wherein R,R$^1$ and R$^6$ are as above,
is treated with an organometallic reagent to yield as metallated pregn-5-en-21-oic acid ester of the formula

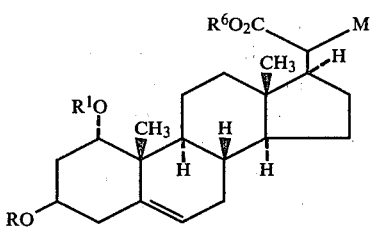

VI wherein R,R$^1$ and R$^6$ are as above and M is lithium, sodium, potassium, magnesium/2 or zinc/2.

For example, the lithium organometallic compound VI may be formed by reaction of the compound of formula V with, for example, lithium diisopropylamide. The sodium organometallic compound VI may be formed by reaction of the compound of formula V with, for example, sodium hexamethyl-disilazane. The potassium organometallic compound VI may be formed by reaction with the compound of formula V with, for example, potassium hydride.

The metallated pregn-5-en-21-oic acid ester of formula VI is preferably generated in situ and is then reacted with a compound of the formula

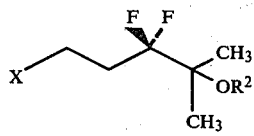

VII wherein X is iodo, bromo, chloro, lower alkyl sulfonyloxy, phenylsulfonyloxy or substituted phenylsulfonyloxy; F is fluorine and R$^2$ is as above, to yield the alkylated compound of the formula

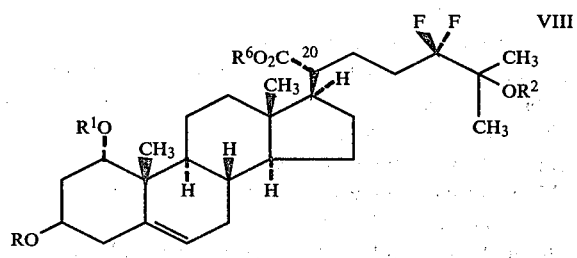

VIII wherein F,R,R$^1$ and R$^6$ are as above.

The aforementioned reaction sequence (V→VI+-VII→VIII) starting with the compound of formula V may be carried out in aprotic inert solvents such as, for example, ethers, for example, diethyl ether, tetrahydrofuran, dimethoxyethane, dioxane and the like; amides, for example, hexamethyl-phosphoramide and the like. Preferred solvents for this purpose are tetrahydrofuran and hexamethylphosphoramide. The use of tetrahydrofuran-hexamethylphosphoramide mixtures is particularly preferred.

The alkylation reaction between a compound of formula VI and formula VII is conveniently carried out at a temperature between −78° C. and 60° C. Most preferably, the alkylation reaction is conducted between a temperature of about −40° C. to 0° C. The desired alkylation product of formula VIII, containing the desired 20R-absolute configuration, can be isolated by the usual chemical and physical means such as chromatography and in this manner can be separated from any undesired impurities such as materials of formula V and VII.

The preparation of a compound of formula VII is set forth below beginning with commercially available 2,2-difluorosuccinic acid of the formula

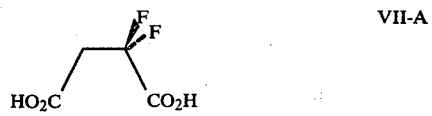

VII-A wherein F is as above.

The diacid of formula VII-A is treated with a 1:1 mixture of an acid anhydride and an organic acid chloride at temperatures in the range of 0° C. to reflux, preferably 0° C. to room temperature so as to yield a cyclic anhydride of the formula

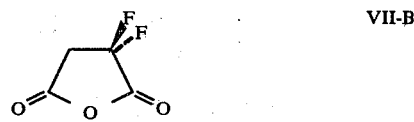

VII-B wherein F is as above.

Among the suitable acid anhydrides for the foregoing reaction are lower aliphatic anhydrides such as acetic anhydride, propionic anhydride, butyric anhydride, isobutyric anhydride and the like. Suitable organic acid chlorides for the foregoing reaction are lower aliphatic acid chlorides such as acetyl chloride, propionyl chloride, butyroyl chloride, isobutyroyl chloride, and the like.

Alternatively, the diacid of formula VII-A could be converted to the cyclic anhydride of formula of VII-B by treatment with either the above mentioned lower aliphatic acid anhydrides or the above mentioned lower aliphatic acid chlorides.

The cyclic anhydride of formula VII-B is selectively opened to the monoester of formula VII-C by reaction with an excess of a lower aliphatic alcohol such as methanol, ethanol, propanol, isopropanol, butanol, isobutanol or an araliphatic alcohol such as benzyl alcohol, or an aromatic alcohol such as phenol and the like. The reaction is carried out at temperatures in the range of 0° C. to reflux preferably 0° C. to 50° C. to yield a compound of the formula

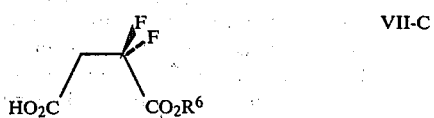

VII-C wherein F and R$^6$ are as above.

The monoester of formula VII-C is selectively reduced with diborane in a lower aliphatic ether solvent such as diethyl ether or ether solvent such as tetrahydrofuran, or borane-dimethyl sulfide complex in a lower aliphatic organic solvent such as hexane and methylene chloride, or inert aromatic solvent such as benzene, toluene and the like, so as to yield the hydroxy ester of formula VII-D. The foregoing reaction is carried out at temperatures in the range of −20° C. to room temperature to yield a compound of the formula

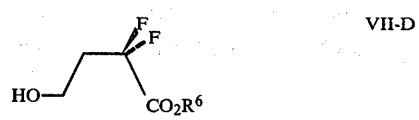

wherein F and $R^6$ are as above.

The hydroxy ester of formula VII-D is converted to the diol of the formula

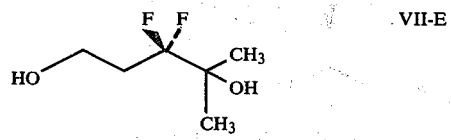

wherein F is as above,
by treatment with excess methyl organometallic reagent such as methyllithium, methylmagnesium chloride, methylmagnesium bromide, methylmagnesium iodide and dimethylmagnesium in ether solent such as diethyl ether and tetrahydrofuran. The foregoing reaction may be carried out at temperatures in the range of −20° C. to 50° C., preferably −10° C. to room temperature.

The diol of formula VII-E is selectively protected by treatment with an acylating agent such as acetic anhydride or benzoyl chloride and an aromatic tertiary amine such as pyridine so as to yield the compound of the formula

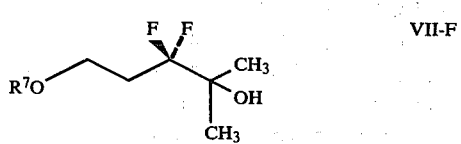

wherein $R^7$ is lower alkanoyl, aralkanoyl or aroyl and F is as above.

The foregoing reaction may be carried out at temperatures ranging from −20° C. to 50° C., preferably −10° C. to room temperature 25° C.

The tertiary alcohol group of formula VII-F is then protected using lower alkyl or aromatic vinyl ethers and p-toluenesulfonic acid catalysts in inert ethers such as diethyl ether or other inert organic solvent such as lower aliphatic hydrocarbons so as to yield an acetal of the formula

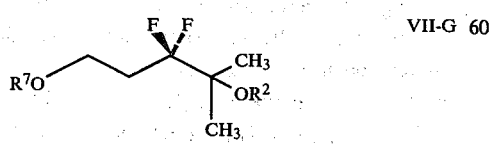

wherein F, $R^2$ and $R^7$ are as above.

Exemplary of lower alkyl vinyl ethers are methyl vinyl ether, ethyl vinyl ether, methyl 1-methylvinyl ether, methyl 2-methylvinyl ether and the like. Exemplary of aromatic ethers are phenyl vinyl ether, phenyl 1-methyl-vinyl ether, phenyl 2-methyl vinyl ether and the like. The aforementioned aromatic ethers may be substituted, and are exemplified by 4-methylphenyl vinyl ether, 4-chlorophenyl vinyl ether, 4-methylphenyl 1-methylvinyl ether and the like. The aforementioned lower alkyl vinyl ethers may include cyclic vinyl ethers(3,4-dihydro-2H-pyrans and 2,3-dihydro-2H-furans).

The ester group of formula VII-G is removed by reduction with lithium aluminum hydride in ether solvents such as diethyl ether or tetrahydrofuran at temperatures in the range of −20° C. to reflux preferably −10° C. to room temperature. This transformation could also be accomplished by a saponification reaction with alkali metal hydroxides such as potassium hydroxide or alkali metal alkoxides such as sodium methoxide in lower aliphatic alcohol or lower aliphatic alcohol-water solvent systems at a temperature range of −20° C. to room temperature to yield an acetal alcohol of the formula

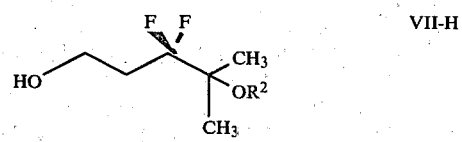

wherein F and $R^2$ are as above.

The acetal alcohol of formula VII-H is then converted to the acetal ester of the formula

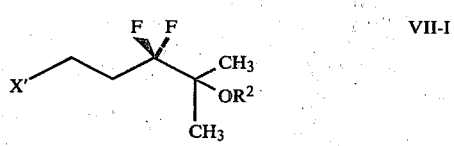

wherein F and $R^2$ are as above and X' is lower alkyl-sulfonyloxy, phenylsulfonyloxy, or substituted phenyl sulfonyloxy with a sulfonyl halide such as p-toluenesulfonyl chloride and an aromatic amine such as pyridine. Other sulfonyl halides such as lower alkyl sulfonyl halides exemplified by methanesulfonyl chloride or aromatic sulfonyl halides exemplified by benzenesulfonyl bromide and p-nitrobenzenesulfonyl chloride may also be used at a temperature range of −20° to 50° C., most preferably at −10° C. to 30° C.

Displacement of the organic sulfonate group in formula VII-I is accomplished by reaction with an alkali metal halide such as sodium iodide in a lower alkyl ketone such as acetone so as to yield the acetal halide of the formula

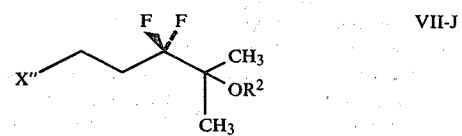

wherein F and $R^2$ are as above and X" is iodo, bromo, or chloro.

The above reaction is preferably carried out with the addition of an acid scavenger such as an hindered tertiary amine base which is exemplified by diisopropyl ethyl amine. This reaction is carried out at temperatures in the range of −20° C. to 50° C., preferably at −10° C. to room temperature. The compounds of formula VII-I and VII-J are encompassed by general formula VII.

Thereafter, the compound of formula VIII is reduced to a compound of the formula

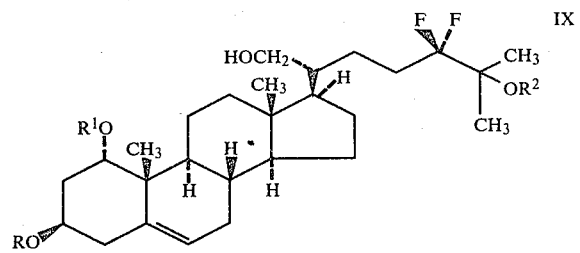

wherein F, R, $R^1$ and $R^2$ are as above, by reduction of the $R^6$ ester grouping of formula VIII with a complex metal hydride reducing agent. Suitable complex metal hydride reducing agents for this purpose include alkali metal aluminum hydrides such as lithium aluminum hydride; mono, di- or tri-(lower alkoxy) alkali metal aluminum hydrides such as, for example, lithium tris(tert-butoxy) aluminum hydride; mono-, di- or tri(lower alkoxy lower alkoxy) alkali metal aluminum hydrides such as, for example, sodium bis(2-methoxyethoxy) aluminum hydride; di(lower alkyl) aluminum hydrides such as, for example, diisobutyl aluminum hydride; and so forth. A particularly-preferred complex metal reducing agent for this purpose is lithium aluminum hydride. Suitable solvents for this reduction include ethers such as diethyl ether, tetrahydrofuran, dimethoxyethane and dioxane. The reduction is conveniently carried out at a temperature between about 0° C. and 100° C., most preferably between about 20° C. and 70° C.

The C-21 alcohol of formula IX is converted in the next step to a C-21 halide or sulfonate ester of the formula

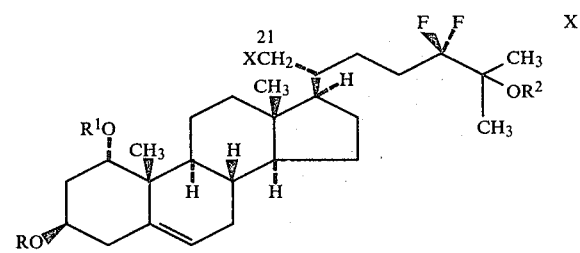

wherein F, R, $R^1$, $R^2$ and X are as above.

The compound wherein X is a p-toluenesulfonyloxy is especially preferred.

To prepare a compound wherein the C-21 substituent is a substituted sulfonyloxy group, one would react the previously-mentioned C-21 alcohol of formula IX with a properly-substituted sulfonyl halide in the presence of a base according to methods known in the art. The preparation of compounds wherein the C-21 substituent is iodo, bromo or chloro can be accomplished either by direct conversion of the C-21 alcohol of formula IX to the desired halo group by means of a halogenating agent such as, for example, phosphorus tribromide, according to methods well known in the art or by reaction of one of the C-21 sulfonate esters with a halide ion containing compound. For example, the C-21 sulfonate ester compound where the ester substituent is tosyloxy may be reacted with an alkali metal bromide or iodide, for example, potassium bromide or potassium iodide, to affod the C-21 halide compound where the halide is bromo or iodo, respectively. All of these interconversions to prepare the C-21 halide and C-21 sulfonate ester compounds are standard in the art for the preparation of primary alkyl halides and sulfonate esters from primary alcohols.

In the next step, the C-21 halide or sulfonate ester of formula X is converted to a compound of the formula

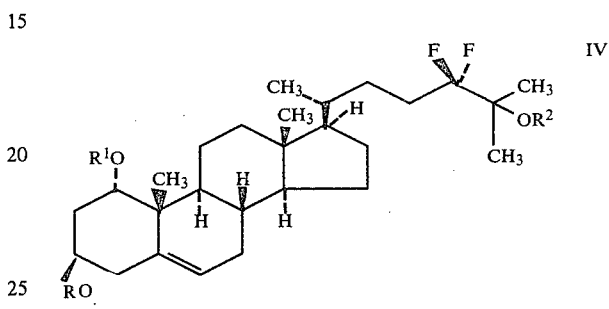

wherein F, R, $R^1$, and $R^2$ are as above, by reaction with a complex metal hydride reducing agent.

Suitable complex metal hydride reducing agents for this purpose include metal aluminum hydrides such as lithium aluminum hydride; mono-, di- or tri(lower alkoxy) alkali metal aluminum hydride such as, for example, lithium tri(tert-butoxy) aluminum hydride; mono-, di- or tri(lower alkoxy lower alkoxy) aluminum metal hydrides such as, for example, sodium bis(2-methoxyethoxy) aluminum hydride; di(lower alkyl) aluminum hydrides such as, for example, diisobutyl aluminum hydride; and so forth. A particularly-preferred complex metal hydride reducing agent for this purpose is lithium aluminum hydride. Suitable solvents for the reduction include ethers such as diethyl ether, tetrahydrofuran, dimethoxyethane and dioxane. The reduction is normally carried out at a temperature between about room temperature and about 100° C., most preferably between about 35° C. and 70° C. Other suitable reducing agents, particularly when the C-21 halide is iodo or bromo, are alkali metal cyanoborohydrides such as, for example, sodium cyanoborohydride (sodium cyanotrihydroborate); tri(lower alkyl) tin hydrides such as tri-n-butyltin hydride; and tri(aryl) tin hydrides such as triphenyltin hydride; and so forth. A particularly-preferred complex metal reducing agent is tri-n-butyltin hydride. Suitable solvents for the reduction include ethers such as diethyl ether, tetrahydrofuran, dimethoxyethane and dioxane. The reduction is normally carried out at a temperature between about −20° C. and 80° C., most preferably between about 0° C. and 40° C.

The cholesterol compound of formula IV is next allylically halogenated to a mixture of 7α- and 7β-halocholesterols of the formula

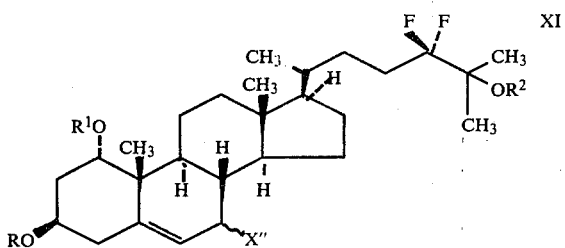

wherein, F, R, $R^1$, $R^2$ and $X''$ are as above.

The halogenation reaction is accomplished using a suitable halogenation agent such as 1,3-dibromo-5,5-dimethylhydantoin, N-chlorosuccinimide, N-iodosuccinimide, N-bromoacetamide and the like dissolved in a saturated aliphatic hydrocarbon or halocarbon such as hexane or carbon tetrachloride in the presence of an acid scavenger such as sodium bicarbonate or sodium carbonate at the boiling point of the reaction medium to give a mixture of $7\alpha$- and $7\beta$-halocholesterols which is used in the following dehydrohalogenation step without separation of the $7\alpha$-halo-isomer from the $7\beta$-isomer.

the $7\alpha$- and $7\beta$-halocholesterol mixture of formula XI is converted to the steroid 5,7-diene of the formula

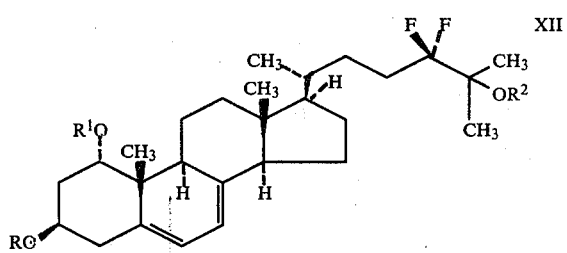

wherein F, R, $R^1$ and $R^2$ are as above;
by a dehydrohalogenation step. The dehydrohalogenation of the crude mixture of $7\alpha$- and $7\beta$-halocholesterols is effected by heteroaromatic and aliphatic tertiary amines, pyridines and alkylated pyridines such as picolines, lutidines and collidines; suitable aliphatic tertiary amines as triethylamine, tripolyamine, 1,5-diazabicyclo (4.3.0) non-5-ene, 1,4-diazabicyclo(2.2.2) octane and the like; s-collidine being preferred. Trialkylphosphites are also useful in the dehydrohalogenation step. Suitable inert organic solvents include aromatic and aliphatic organic solvents such as benzene, toluene, xylene, decalin and the like. Xylene is the preferred solvent. The reaction proceeds readily at temperatures from about 50° C. to the reflux temperature of the reaction medium, most readily at the reflux temperature of the solvent system. The desired steroid 5,7-diene of formula XII can be isolated by the usual chemical and physical means such as chromatography and in this manner can be separated from any undesired impurities.

In the next step, the steroid 5,7-diene of formula XII is converted into the protected precholecalciferol compound of the formula

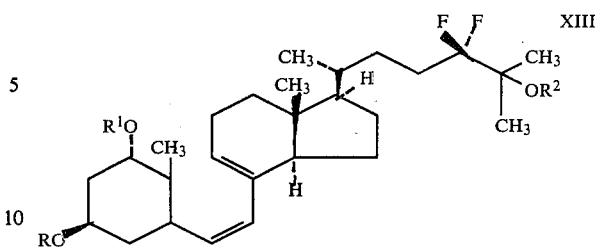

wherein F, R, $R^1$ and $R^2$ are as above;
by irradiation under an inert atmosphere by means of a mercury lamp equipped with a glass cooling finger at a temperature range of about $-40°$ C. to about 25° C., about $-20°$ C. to about 10° C. being the preferred irradiation temperature range for the period of time necessary to effect about 50% conversion of the starting material. Suitable inert atmospheres include nitrogen, helium, argon and the like. Suitable source of irradiation energy include high- and low-pressure mercury, xenon-mercury and thallium-mercury lamps. High-pressure mercury lamps are preferred. A 450 W Hanovia high-pressure mercury lamp is the most preferred source of irradiation energy. Suitable inert organic solvent systems for the irradiation include mixtures of saturated aliphatic hydrocarbons such as pentane, hexane, isooctane and the like and ethereal solvents such as diethyl ether, dimethoxyethane, tetrahydrofuran, dioxane and the like. Preferred mixtures contain hexane and tetrahydrofuran.

Upon completion of the irradiation, the solvents are removed by evaporation, and the residue is separated into the pure protected precholecalciferol of formula XIII and pure unchanged steroid 5,7-diene of formula XII on a high-performance liquid chromatography column using a solid absorbent and an inert organic eluant. Suitable organic eluants for the separation step include mixtures of hydrocarbons such as n-hexane, isooctane, cyclohexane and the like and esters such as ethyl acetate, ethyl formate and the like. Suitable solid absorbents include Porasil, Corasil, Biosil, Zorbax, Zorbax-Sil, Sil-X and the like. A Waters Associates Chromatograph Model 202 using an four-foot by 1-inch Porasil A column and a mixture of n-hexane:ethyl acetate as the eluant is the preferred high-performance liquid chromatographic system.

Unchanged, 5,7-diene of formula XII is recycled through the irradiation process to obtain additional quantities of pure protected precholecalciferol of formula XIII thereby rendering this crucial step of the process and the overall process highly efficient in comparison with related processes previously disclosed, for example, by D. H. R. Barton et al., *J. Chem. Soc. Chem., Comm.* (1974)203 and by H. F. DeLuca et al., *Tetrahedron Lett.* (1972)4417.

The protected precholecalciferol of formula XIII is rearranged thermally to the protected cholecalciferol of the formula

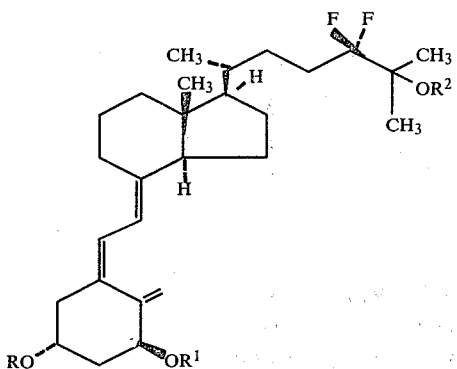

wherein F, R, $R^1$ and $R^2$ are as above,
by heating at 50°–100° C. the protected precholecalciferol of formula XIII in an inert solvent such as the ethers, dioxane, tetrahydrofuran, dimethoxyethane and the like; and the aromatic hydrocarbons such as benzene and toluene and the like, and aliphatic hyrocarbons such as hexane and heptane and the like; under an inert atmosphere such as argon, helium, nitrogen and the like by methods known in the art. See, for example, D. H. R. Barton, et al., *J. Amer. Chem. Soc.* 98(1973)2748.

Finally, removal of the protecting groups R, $R^1$, and $R^2$ of the protected cholecalciferol of formula II gave 24,24-difluoro-1α,25-dihydroxycholecalciferol of the formula

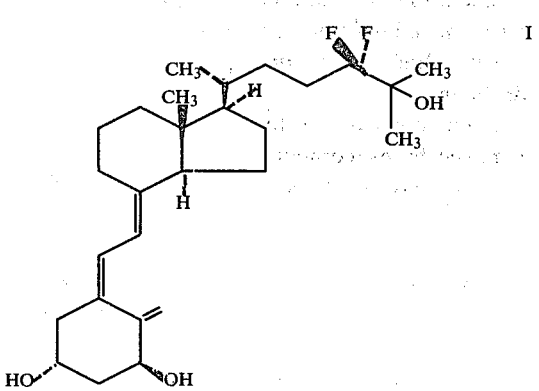

wherein F is as above,
by treatment with an acid in a protic solvent. Suitable acids include mineral acids such as hydrochloric or sulfuric acid and the like, organic acids such as p-toluenesulfonic acid, trifluoroacetic acid and the like, and cationic exchange resins in the hydrogen form such as Bio-Rad AG 50 W-X4, Bio-Rad Ag 50 W, Dowex 50 W, Duolite C20, Amberlite IR and the like. Cationic exchange resins in the hydrogen form are preferred. Bio-Rad 50 W-X4 is most preferred. Suitable protic solvents include the alkanols, methanol, ethanol, 2-propanol and the like, and alkandiols such as ethylene glycol, propylene glycol and the like, and water mixed with a miscible cosolvent to help solubilize the organic reactants, for example, ethers such as tetrahydrofuran or dimethoxyethane; or a ketone such as acetone. Alkanols are preferred, methanol is most preferred. It is preferable to carry out the removal of the protecting groups at a temperature between about −10° C. and about 80° C., most preferably between about 0° C. and 40° C.

Alternatively, the blocking groups can be removed to give the compound of formula I by treating the protected cholecalciferol of formula II with a tri-lower alkylsilyl iodide in an inert organic solvent such as hexane, or methylene chloride or an aromatic solvent such as benzene or toluene at about −20° C. to the reflux temperature of the solvent, preferably at about 0° C.–50° C. under an inert atmosphere.

By an alternative sequence the substituted cholesterol derivatives of formula

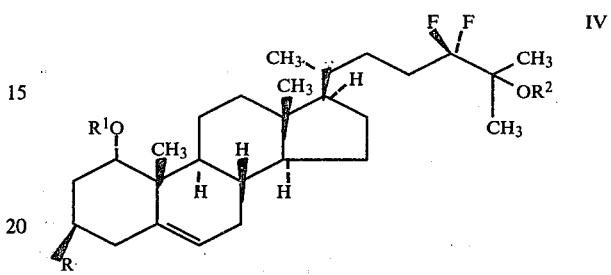

wherein F, R, $R^1$, and $R^2$ are as above
are deprotected by removal of the protecting groups with a strong acid in a protic solvent or with a tri-lower alkylsilyl iodide so as to yield 1α,3β-24,24-difluorocholest-5-en-1,3,25-triol of the formula

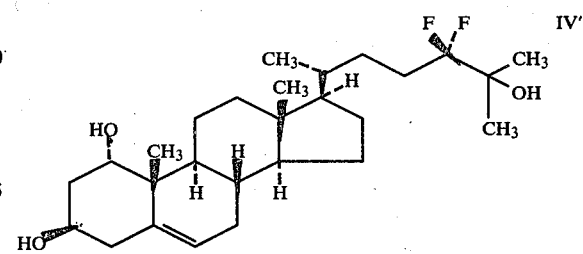

wherein F is as above.
Suitable strong acids for this purpose include mineral acids such as hydrochloric or sulfuric acid; and organic sulfonic acids such as p-toluenesulfonic acid. Suitable protic solvents include alcohols such as methanol and ethanol. It is preferable to carry out the removal of the aforementioned protecting groups at a temperature between about −10° C. and about 80° C., most preferably between about 0° C. and 40° C. Suitable tri-lower alkylsilyl iodides include trimethylsilyl iodide in an inert organic solvent such as hexane or methylene chloride, or an aromatic solvent such as benzene or toluene at −20° C. to the reflux temperature of the solvent, preferably at 0° C.–50° C. under an inert atmosphere.

The 1α,3β-24,24-difluorocholest-5-en-1,3,25-triol of formula IV' is then alkanoylated to the compound of the formula

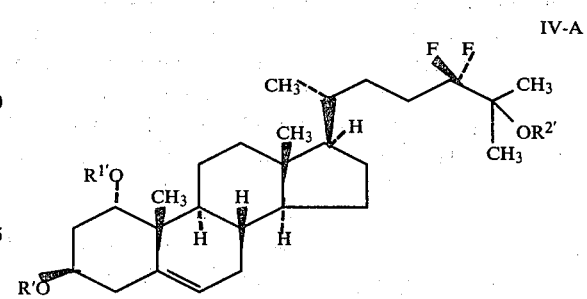

wherein F, R', R¹', and R²' are as above,
by methods well known in the art. For example, to selectively diacylate the 1α- and 3β-hydroxy groups of compound IV' to give IV-A, one may employ an acylating agent such as acetic anhydride, phenyl acetyl chloride or benzoyl chloride and triethylamine or pyridine solvent at temperatures in the range of about −10° C. to about 50° C., most preferably at a temperature from 0° C.-30°.

The 1α,3β-24,24-difluorocholest-5-en-1,3,25-triol of formula IV' can also be triacylated to a compound of the formula IV-A by employing the above-mentioned acylating agents, solvents, and reaction temperatures and employing a catalytic amount of 4-dimethylaminopyridine catalyst or by heating the above reaction mixtures to 100°-150° with excess acylating agent.

The substituted cholesterol derivatives of formula IV-A are next allylically halogenated to a mixture of 7α- and 7β-halocholesterols of the formula

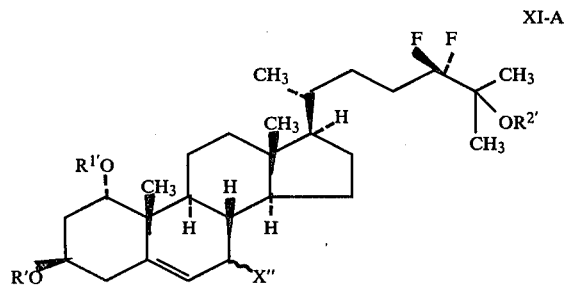

XI-A wherein F, R, R',R¹', R²' and X'' are as above.

The halogenation reaction ia accomplished using a suitable halogenation agent such as 1,3-dibromo-5,5-dimethylhydantoin, N-chlorosuccinimide, N-iodosuccinimide, N-bromoacetamide and the like dissolved in a saturated aliphatic hydrocarbon or halocarbon such as hexane or carbon tetrachloride in the presence of an acid scavenger such as sodium bicarbonate or sodium carbonate at the boiling point of the reaction medium to give a mixture of 7α- and 7β-halocholesterols which is used in the following dehydrohalogenation step without separation of the 7α-halo-isomer from the 7β-isomer.

The 7α- and 7β-halocholesterol mixture of formula XI-A is converted to the steroid 5,7-diene of the formula

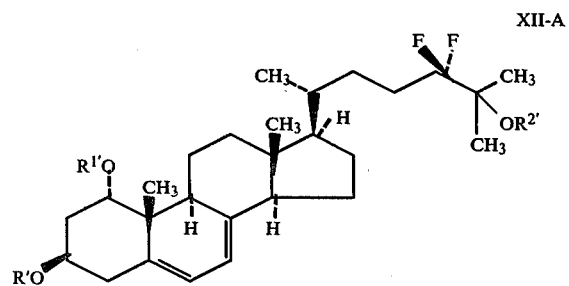

XII-A wherein F, R', R¹', and R²' are as above,
by a dehydrohalogenation step. The dehydrohalogenation of the crude mixture of 7α- and 7β-halocholesterols is effected by heteroaromatic and aliphatic tertiary amines, pyridines and alkylated pyridines such as picolines, lutidines and collidines; suitable aliphatic tertiary amines are triethylamine, tripropylamine, 1,5-diazabicyclo (4.3.0) non-5-ene, 1,4-diazabicyclo (2.2.2) octane and the like; s-collidine being preferred. Trialkylphosphites are also useful in the dehydrohalogenation step. Suitable inert organic solvents include aromatic and aliphatic organic solvents such as benzene, toluene, xylene, decalin and the like. Xylene is the preferred solvent. The reaction proceeds readily at temperatures from about 50° C. to the reflux temperature of the reaction medium, most readily at the reflux temperature of the solvent system. The desired steroid 5,7-diene of formula XII-A can be isolated by the usual chemical and physical means such as chromatography and in this manner can be separated from any undesired impurities.

In the next step, the steroid 5,7-diene of formula XII-A is converted into the protected precholecalciferol compound of the formula

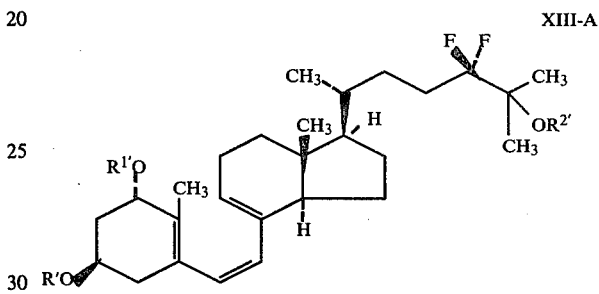

XIII-A wherein F, R', R¹', and R²' are as above,
by irradiation under an inert atmosphere by means of a mercury lamp equipped with a glass cooling finger at a temperature range of about −40° C. to about 25° C., about −20° C. to about 10° C. being the preferred irradiation temperature range for the period of time necessary to effect about 50% conversion of the starting material. Suitable inert atmospheres include nitrogen, helium, argon and the like. Suitable source of irradiation energy include high- and low-pressure mercury, xenon-mercury and thallium-mercury lamps. High-pressure mercury lamps are preferred. A 450 W Hanovia high-pressure mercury lamp is the most preferred source of irradiation energy. Suitable inert organic solvent systems for the irradiation include mixtures of saturated aliphatic hydrocarbons such as pentane, hexane, isooctane and the like and ethereal solvents such as diethyl ether, dimethoxyethane, tetrahydrofuran, dioxane and the like. Preferred mixtures contain hexane and tetrahydrofuran.

Upon completion of the irradiation, the solvents are removed by evaporation, and the residue is separated into the pure protected precholecalciferol of formula XIII-A and pure unchanged steroid 5,7-diene of formula XII-A on a high-performance liquid chromatography column using a solid absorbent and an inert organic eluant. Suitable organic eluants for the separation step include mixtures of hydrocarbons such as n-hexane, isooctane, cyclohexane and the like and esters such as ethyl acetate, ethyl formate and the like. Suitable solid absorbents include Porasil, Corasil, Biosil, Zorbax, Zorbax-Sil, Sil-X and the like. A Waters Associates Chromatograph Model 202 using a four-foot by 1-inch Porasil A column and a mixture of n-hexane:ethyl acetate as the eluant is the preferred high-performance liquid chromatographic system.

Unchanged, 5,7-diene of formula XII-A is recycled through the irradiation process to obtain additional quantities of pure protected precholecalciferol of formula XIII-A thereby rendering this crucial step of the process and the overall process highly efficient in comparison with related processes previously disclosed, for example, by D. H. R. Barton et al., *J. Chem. Soc. Chem. Comm.* (1974) 203 and by H. F. DeLuca et al., *Tetrahedron Lett.* (1972) 4417.

The protected precholecalciferol of formula XIII-A was rearranged thermally to the protected cholecalciferol of the formula

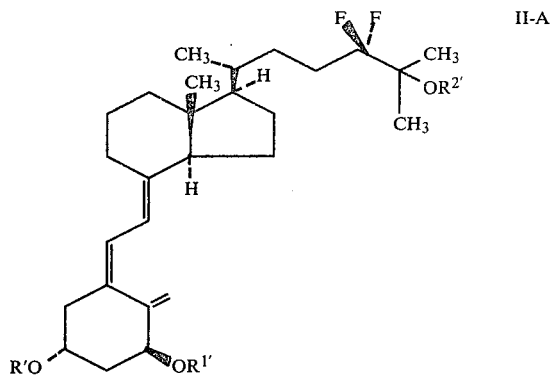

II-A wherein F, R', R$^{1'}$, and R$^{2'}$ are as above, by heating at 50° C.–100° C. the protected precholecalciferol of formula XIII-A in an inert solvent such as the ethers, dioxane, tetrahydrofuran, and the like, the aromatic hydrocarbons such as benzene, toluene and the like and aliphatic hydrocarbons like hexane, heptane and the like under an inert atmosphere such as argon, helium or nitrogen and the like by methods known in the art. See, for example, D. H. R. Barton, *J. Amer. Chem. Soc.*, 98 (1973) 2748.

The last step in this particular sequence involves the saponification of the compound of formula II-A to give 24,24-difluoro-1α,25-dihydroxycholecalciferol of the formula

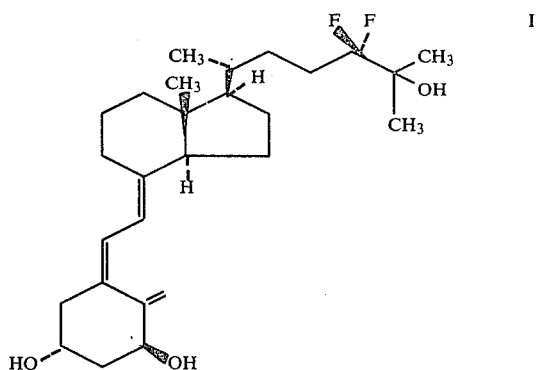

I wherein F is as above.

The saponification of the compound of formula II-A is conducted by treatment with strong bases in protic solvents to yield the compound of formula I. Suitable bases include alkali and alkaline earth hydroxides, alkoxides such as methoxide, ethoxide and the like. Potassium hydroxide is most preferred. Suitable solvents include alcohols such as methanol and ethanol and water containing a miscible cosolvent to help solubilize the organic reactants, for example, an ether such as tetrahydrofuran or dimethoxyethane. Methanol is most preferred. It is preferable to carry out the removal of the protecting groups R', R$^{1'}$ and R$^{2'}$ of formula II-A at a temperature between about −20° C. and about 60° C., most preferably between about −5° C. and 30° C. It is also preferable to perform the saponification under an inert atmosphere of nitrogen, argon and the like.

The protected precholecalciferol of formula XIII-A is saponified to the precholecalciferol of the formula

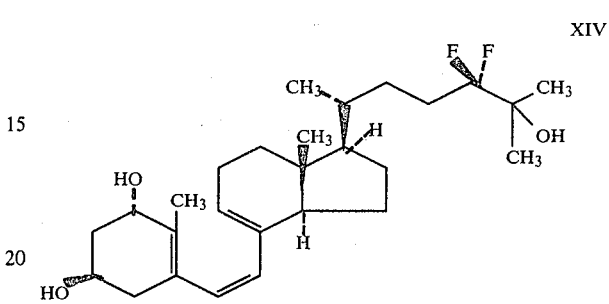

XIV wherein F is as above.

The saponification of the compound of formula XIII-A is conducted by treatment with strong bases in protic solvents to yield the compound of formula XIV. Suitable bases include alkali and alkaline earth hydroxides, alkoxides such as methoxides, ethoxides and the like. Potassium hydroxide is most preferred. Suitable solvents include alcohols such as methanol and ethanol and water containing a miscible cosolvent to help solubilize the organic reactants, for example, an ether such as tetrahydrofuran or dimethoxyethane. Methanol is most preferred. It is preferable to carry out the removal of the protecting groups R', R$^{1'}$ and R$^{2'}$ of formula XIII-A at a temperature between about −20° C. and about 60° C., most preferably between about −5° C. and 30° C. It is also preferable to perform the saponification under an inert atmosphere of nitrogen, argon and the like.

The last step in this sequence involves the thermal isomerization of precholecalciferol of formula XIV to give 24,24-difluoro-1,25-dihydroxycholecalciferol of the formula

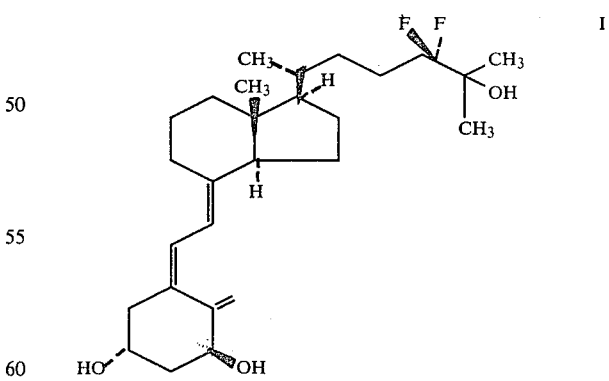

I wherein F is as above,
by heating at 50° C.–100° C. the precholecalciferol of formula XIV in an inert solvent such as the ethers, dioxane, tetrahydrofuran, dimethoxyethane and the like; the aromatic hydrocarbons such as benzene, toluene, and the like under an inert atmosphere such as argon, helium or nitrogen and the like by methods well known in the art. See, for example, D. H. R. Barton et al., *J. Amer. Chem. Soc.* 98 (1973) 2748.

24,24-difluoro-1,25 dihydroxycholecalciferol has shown activity in the anti-rachitogenic test in chicks, the diphosphonate procedure in rats, and in reduction of epiphyseal plate width in normal mice. The difluoro compound also has a long duration of activity in stimulation of intestinal calcium absorption (96 hours after a single oral 100 nanogram dose).

(a) Anti-Rachitogenic Activity in Chicks

One-day-old White Leghorn cockerels are placed on a vitamin D-deficient diet which contains 1% calcium and 0.7% phosphorous and are housed under ultraviolet-free lighting (General Electric F40G0 gold fluorescent lights). Compounds are dissolved in propylene glycol and administered orally in a volume of 0.2 ml for 21 consecutive days to chicks which are one to two days of age at the start of treatment. Controls are treated with vehicle alone. Compounds are prepared in amber flasks and the solutions are flushed with argon and refrigerated after each dosing period. Chicks are autopsied on the day after the last treatment day. Blood is collected for determination of serum calcium and phosphorus and tibia dry weight and ash weight are determined. Usually, ten chicks are used for each treatment group and for the control group. The results of the anti-rachitogenic activity assay are shown in Table I. The results show that 24,24-difluoro-1,25 dihydroxycholecalciferol possess potent anti-rachitogenic activity.

TABLE I
ANTI-RACHITOGENIC ACTIVITY OF
24,24-DIFLUORO-1α,25-DIHYDROXY
CHOLECALCIFEROL IN CHICKS

| DOSE NG/CHICK/DAY | MEAN TIBIA ASH WEIGHT (MG) ± S.E. 24,24-difluoro-1α,25-dihydroxy-cholecalciferol |
|---|---|
| 0 | 120.7 ± 5.9 |
| 1 | 111.7 ± 5.8 NS |
| 3 | 151.5 ± 4.7*** |
| 10 | 227.1 ± 8.2*** |
| 30 | 244.8 ± 7.4*** |

21 DAYS ORAL DOSING
9-10 CHICKS PER GROUP
***STATISTICAL SIGNIFICANT RESULTS
NS — NOT STATISTICALLY SIGNIFICANT (b) Intestinal Calcium Absorption in Chicks White Leghorn one-day-old cockerels are placed on the vitamin D-deficient diet and are housed under ultraviolet-free lighting for 21 days. Chicks are then used to determine the effects of test compounds on intestinal calcium absorption. A single oral dose of test compound dissolved in propylene glycol is administered. At various times after dosing, 2 uCi of $^{45}Ca$ (chloride) is given orally, and serum radioactivity is measured 45 minutes after administration of the isotope. Ten chicks are used in each treatment and control group and vehicle-treated controls are included at each time period. The results of the intestinal calcium absorption assay are shown in Table II. The results show that 24,24-difluoro-1α,25-dihydroxycholecalciferol has potent intestinal calcium absorption activity of long duration.

TABLE II
EFFECT OF 24,24-DIFLUORO-1α,
25-DIHYDROXY CHOLECALCIFEROL ON
$^{45}CA$ ABSORPTION IN VITAMIN D-DEFICIENT CHICKS

| TREATMENT (ORAL) | TIME (HR) | NO. OF CHICKS | SERUM $^{45}CA$ CPM/0.2 ML |
|---|---|---|---|
| VEHICLE, 0.2 ML | 24 | 11 | 992 ± 81 |
| 24,24 DIFLUORO-1α,25-DIHYDROXY-CHOLECALCIFEROL 0.1 MCG | | 11 | 2064 ± 170*** |
| VEHICLE, 0.2 ML | 48 | 11 | 769 ± 90 |
| 24,24-DIFLUORO-1α,25-DIHYDROXY-CHOLECALCIFEROL 0.1 MCG | | 11 | 1539 ± 99*** |
| VEHICLE, 0.2 ML | 72 | 10 | 647 ± 69 |
| 24,24-DIFLUORO-1α,25-DIHYDROXY-CHOLECALCIFEROL 0.1 MCG | | 11 | 1164 ± 90*** |
| VEHICLE, 0.2 ML | 96 | 10 | 586 ± 70 |
| 24,24-DIFLUORO-1α,25-DIHYDROXY-CHOLECALCIFEROL 0.1 MCG | | 10 | 998 ± 61*** |
| VEHICLE, 0.2 ML | 120 | 16 | 566 ± 39 |
| 24,24-DIFLUORO-1α,25-DIHYDROXY-CHOLECALCIFEROL 0.1 MCG | | 15 | 642 ± 38 NS |
| VEHICLE, 0.2 ML | 144 | 16 | 696 ± 54 |
| 24,24-DIFLUORO-1α,25-DIHYDROXY-CHOLECALCIFEROL 0.1 MCG | | 16 | 672 ± 38 NS |

***STATISTICALLY SIGNIFICANT RESULTS
NS — NOT STATISTICALLY SIGNIFICANT (c) Prevention of EHDP-Induced Mineralization Block in Rats Charles River CD male rats are treated for 10 consecutive days. Rats are 21 days of age at the start of treatment. The disodium salt of ethane-1-hydroxy-1,1-diphosphonate (EHDP) is given subcutaneously on each treatment day at a dose of 2 mg/0.2 ml/rat in distilled water. Test compounds are administered orally on each treatment day in propylene glycol (0.2 ml/rat). Rats are autopsied on the day after the last treatment day and tibias are processed by a modified von Kossa procedure based upon silver impregnation of bone salts. Epiphyseal plate widths are measured with a micrometer ocular using standard microscopic magnification (35 x). Activity is based upon dose-dependent narrowing of the widened epiphyseal plate induced by EHDP. Ten rats are used in each treatment group. Positive (EHDP alone) and negative (vehicles alone) control groups of ten rats each are included in each experiment. The results of the assay are shown in Table III. The results show that 24,24-difluoro-1α,25-dihydroxycholecalciferol calcified the tibial epiphyseal plate in EHDP-blocked rats.

TABLE III
EFFECTS OF 24,24-DIFLUORO-1α,25-DIHYDROXY
CHOLECALCIFEROL IN EHDP-TREATED RATS

| DOSE NG/RAT/DAY | MEAN TIBIA EPIPHYSEAL PLATE WIDTH (MICRA) ± S.E. 24,24-DIFLUORO-1α,25-DIHYDROXY-CHOLECALCIFEROL |
|---|---|
| 0 | 1182 ± 51 |
| 1 | 839 ± 18*** |
| 3 | 674 ± 18*** |
| 10 | 540 ± 16*** |

TABLE III-continued

EFFECTS OF 24,24-DIFLUORO-1α,25-DIHYDROXY CHOLECALCIFEROL IN EHDP-TREATED RATS

| DOSE NG/RAT/DAY | MEAN TIBIA EPIPHYSEAL PLATE WIDTH (MICRA) ± S.E. 24,24-DIFLUORO-1α,25-DIHYDROXY-CHOLECALCIFEROL |
|---|---|
| 30 | 412 ± 9*** |
| VEHICLE CONTAINS (NO EHDP) | 440 ± 2 |

10 DAYS ORAL DOSING
10 RATS PER GROUP
***STATISTICAL SIGNIFICANT RESULTS

The compound of formula I can be administered in dosages that are in the range of about 50–100 nanograms per day for the treatment of such disease states as osteodystrophy, steroid induced osteopenia, hypoparathyroidism, hypophosphatemic rickets and hypophosphatemic ostemalacia which are characterized by lower than normal levels of endogenously produced 1,25-dihydroxycholecalciferol. The compound of formula I can be administered orally, subcutaneously, intramuscularly, intravenously, or intraperitoneally.

The compound of formula I can be formulated into compositions such as tablets, capsules, and the like, or elixers for oral administration, or in sterile solutions or suspensions for parenteral administration. About 50–200 nanograms of the compound of formula I is compounded with a pharmaceutically acceptable vehicle, carrier, excipient, binder, preservative, stabilizer, flavor, and the like, in a unit dosage as called for by accepted pharmaceutical practice. The amount of active substance in the foregoing compositions or preparations is in the range previously indicated.

Illustrative of the adjuvants which may be incorporated into capsules, and the like are the following: a binder such as gum tragacanth, acacia, corn starch, or gelatin; an excipient such as dicalcium phosphate; a disintegrating agent such as corn starch, potato starch, algenic acid, and the like; a lubricant such as magnesium stearate, a sweetening agent such as sucrose, lactose, or saccharin; a flavoring agent such as peppermint, oil of wintergreen, or cherry. Various other materials may be present as coatings or to otherwise modify the physical form of the dosage unit. For instance, tablets may be coated with shallac, sugar, or both. A syrup or elixir may contain the active compound, sucrose as a sweetening agent, methyl and propyl parabens as preservatives, a dye, and in flavoring such as cherry or orange flavor.

Sterile compositions for injection can be formulated according to conventional pharmaceutical practice by dissolving or suspending the active substance in a vehicle, such as water for injection, a naturally-occurring vegetable oil, such as sesame oil, coconut oil, peanut oil, cottonseed oil, and the like, or a synthetic fatty vehicle such as ethyl oleate or the like. Buffers, preservatives, antioxidants and the like can be incorporated as required.

The Examples which follow further illustrate the invention. All temperatures are in degrees Centigrade unless otherwise stated.

EXAMPLE 1

To a solution of 10.8 mL of acetic anhydride and 10.8 mL of acetyl chloride at 0° C. was added 10.80 g (0.070 mol) of 2,2-difluorosuccinic acid in several portions. The mixture was heated for 1 hr at 50° C. and cooled. The reaction was concentrated under reduced pressure to yield 2,2-difluorosuccinic anhydride. NMR (CDCl$_3$) δ3.56 ppm (triplet, 2, J=15 Hz).

EXAMPLE 2

To 9.25 g (0.068 mol) of 2,2-difluorosuccinic anhydride at 0° C. was added dropwise 30 mL of dry absolute ethanol. The mixture was allowed to warm to 25° and was stirred for 18 hr. The mixture was evaporated under reduced pressure to yield ethyl 2,2-difluoro-3-carboxypropionate. NMR (CDCl$_3$) δ7.20 (broad, 1), 4.35 (quartet, 2, J=7 Hz), 3.31 (triplet, 2, J=14 Hz), and 1.36 ppm (triplet, 3, J=7 Hz).

EXAMPLE 3

A solution of 123.0 mL (0.123 mol) of 1.0 M of borane in tetrahydrofuran was added dropwise at 0° to a mixture of 12.4 g (0.068 mol) of ethyl 2,2-difluoro-3-carboxypropionate in 70 mL of dry tetrahydrofuran. The reaction mixture was stirred at 0° for 18 hr then was quenched by adding 40 mL of water dropwise. The solution was saturated with solid sodium chloride and the product was isolated with ether. The ether layers were washed with saturated aqueous sodium bicarbonate and brine. The solution was dried over anhydrous magnesium sulfate, filtered, and evaporated to dryness to yield ethyl 2,2-difluoro-4-hydroxybutyrate. NMR (CDCl$_3$) δ4.32 (quartet, 2, 2, J=7 Hz), 3.87 (triplet, 2, J=6 Hz), 2.36 (multiplet, 2) and 1.35 ppm (triplet, 3, J=7 Hz).

EXAMPLE 4

To a solution of 311 mL of 1.6 M ethereal methyllithium (0.498 mol) of 0° was added dropwise 11.16 g (0.066 mol) of ethyl 2,2-difluoro-4-hydroxybutanoate in 150 mL of ether. The mixture was stirred at 0° C. for 1 hr and at 25° C. for 17 hr. The mixture was quenched by adding 14 mL of saturated brine at 0° C. The mixture was poured into saturated brine and the product was isolated with ether. The ether layers were dried over anhydrous magnesium sulfate, filtered, and evaporated to dryness. The residue was chromatographed on 0.06–0.20 mm of silica gel to give 4-methyl-3,3-difluoro-1,4-pentanediol. NMR (CDCl$_3$) δ3.84 (triplet, 2, J=6 Hz), 2.75 (broad, OH), 2.22 (multiplet, 2), and 1.31 ppm (triplet, 6, J=1 Hz).

EXAMPLE 5

To a mixture of 6.92 g (0.045 mol) of 4-methyl-3,3-difluoro-1,4-pentanediol and 28 mL of pyridine at 0° C. was added 16 mL of acetic anhydride and the mixture was stirred at 0° C. for 1 hr and at 25° C. for 1 hr. The mixture was added to 15 mL of methanol and the solution was evaporated to dryness to yield oily 4-methyl-3,3-difluoro-1,4-pentanediol 1-acetate. NMR (CDCl$_3$) δ4.40 (triplet, 2, J=7 Hz), 2.30 (multiplet, 2), 2.06 (singlet, 3) and 1.33 ppm (triplet, 6, J=1 Hz).

EXAMPLE 6

A mixture of 7.77 g (0.040 mol) of 4-methyl-3,3-difluoro-1,4-pentanediol 1-acetate, 74 mL of ethyl vinyl ether and 0.50 g of p-toluenesulfonic acid monohydrate were stirred at −45° C. for 1 hr. The mixture was quenched by adding 11 mL of triethylamine and evaporated to dryness. The residue was taken up in ether. This solution was successively washed with saturated aqueous sodium bicarbonate solution and saturated brine. The ether phase was dried over anhydrous magnesium sulfate, filtered and evaporated to dryness to yield an oil containing 4-(1-ethoxyethoxy)-3,3-difluoro-4-methyl-1-pentanol 1-acetate.

EXAMPLE 7

To a mixture of 2.25 g (0.059 mol) of lithium aluminum hydride in 50 mL of ether at 0° C. was added dropwise, 11.30 g (0.040 mol) of 4-(1-ethoxyethoxy)-3,3-difluoro-4-methyl-1-pentanol 1-acetate in 130 mL of ether. The mixture was heated at reflux (35° C.) for 3 hr and then was recooled to 0° C. The mixture was quenched by adding dropwise 4.5 mL of water followed by 3.6 mL of 10% aqueous sodium hydroxide. The mixture was stirred at 25° C. for 0.5 hr and was filtered. Evaporation of solvent and column chromatography of the residue on 0.06–0.20 mm silica gel afforded 4-(1-ethoxyethoxy)-3,3-difluoro-4-methyl-1-pentanol. NMR (CDCl$_3$) $\delta$5.00 (quartet, 1, J=7 Hz), 3.86 (broad, 2), 3.51 (quartet, 2, J=7 Hz), 2.25 (multiplet, 2), 1.35 (triplet, 6, J=1 Hz), 1.30 (doublet, 3, J=7 Hz), and 1.18 ppm (triplet, 3, J=7 Hz).

EXAMPLE 8

A mixture of 1.00 g (0.0044 mol) of 4-(1-ethoxyethoxy)-3,3-difluoro-4-methyl-1-pentanol, 4 mL of pyridine and 1.27 g (0.0066 mol) of p-toluenesulfonyl chloride was stirred at 0° C. for 18 hr. The mixture was quenched with ice chips. The mixture was then poured into water and extracted with methylene chloride. The organic phase was sequentially washed with 10% aqueous sulfuric acid and saturated aqueous sodium bicarbonate solution. The organic phase was dried over anhydrous magnesium sulfate, filtered and evaporated to dryness to yield oily 4-(1-ethoxyethoxy)-3,3-difluoro-4-methyl-1-pentanol 1-(4-methylbenzenesulfonate). NMR (CDCl$_3$) $\delta$4.93 (quartet, 1, J=7 Hz), 4.27 (triplet, 2, J=7 Hz), 3.45 (quartet, 2, J=7 Hz), 2.45 (singlet, 3), 2.36 (multiplet, 2), 1.27 (triplet, 6, J=1 Hz), 1.24 (doublet, 3 J=7 Hz), and 1.15 ppm (triplet, 3, J=7 Hz).

EXAMPLE 9

A mixture of 3.50 g (0.0087 mol) of 4-(1-ethoxyethoxy)-3,3-difluoro-4-methyl-1-pentanol 1-(4-methylbenzenesulfonate), 40 mL of acetone, 0.5 mL of diisopropylethylamine and 13.10 g (0.087 mol) of sodium iodide was stirred at 25° C. for 64 hr. The mixture was evaporated to dryness. The residue was partitioned between 5% aqueous sodium sulfite solution and methylene chloride. The organic phase was washed with saturated aqueous sodium bicarbonate solution. The organic phase was then dried over anhydrous magnesium sulfate, filtered, and evaporated to dryness. The residue was chromatographed on 0.06–0.20 mm silica gel to yield 4-(1-ethoxyethoxy)-3,3-difluoro-1-iodo-4-methylpentane. NMR (CDCl$_3$) $\delta$4.98 (quartet, 1, J=7 Hz), 3.50 (quartet, 2, J=7 Hz), 3.28 (multiplet, 2), 2.60 (multiplet, 2), 1.32 (triplet, 6, J=1 Hz), 1.28 (doublet, 2, J=7 Hz), and 1.18 ppm (triplet, 3, J=7 Hz).

EXAMPLE 10

A mixture of 0.91 g (0.0030 mol) of 1$\alpha$,3$\beta$-dihydroxyandrost-5-en-17-one [R. M. Dodson, A. H. Goldkamp and R. D. Muir, J. Amer. Chem. Soc., 82, 4026 (1960)], 15 mL of tetrahydrofuran, 1.26 g (0.015 mol) of 3,4-dihydro-2H-pyran and 0.028 g of p-toluenesulfonic acid monohydrate was stirred at 25° for 18 hr. The mixture was diluted with methylene chloride. This solution was then washed with saturated aqueous sodium bicarbonate solution. The organic phase was dried over anhydrous magnesium sulfate, filtered and evaporated to dryness to yield oily [1$\alpha$,3$\beta$]-1,3-bis[(tetrahydro-2H-pyran-2-yl)oxy]androst-5-eh-17-one, [$\alpha$]$_D^{20}$+34.3° (c 1, CHCl$_3$).

EXAMPLE 11

To a mixture of 1.00 g (0.0021 mol) of [1$\alpha$,3$\beta$]-1,3-bis[(tetrahydro-2H-pyran-2-yl)oxy]androst-5-en-17-one, 1.94 g (0.0087 mol) of triethyl phosphonoacetate, and 14 ml of ethyl alcohol was added 0.68 g (0.010 mol) of sodium ethoxide in 7 mL of ethanol. The mixture was stirred at reflux (80° C.) for 18 hr and cooled. The mixture was concentrated under reduced pressure. The residue was partitioned between water and ether and the organic phase was washed with saturated brine. The organic phase was then dried over anhydrous magnesium sulfate, filtered, and evaporated to dryness. The residue was chromatographed on 0.06–0.20 mm silica gel to yield [1$\alpha$,3$\beta$,17(20)E]-1,3-bis[(tetra-2H-pyran-2-yl)oxy]pregna-5,17(20)-dien-21-oic acid ethyl ester [$\alpha$]$_D^{20}$−8° (c 1, CHCl$_3$).

EXAMPLE 12

A mixture of 0.32 g (0.00059 mol) of [1$\alpha$,3$\beta$,17(20E)]-1,3-bis[(tetrahydro-2H-pyran-2-yl)oxy]pregna-5,17(20)-dien-21-oic acid ethyl ester, 0.10 g of platinum oxide, and 20 mL of ethanol was stirred in 1 atmosphere of hydrogen for 2 hr. The mixture was filtered through a pad of diatomaceous earth and the solids were washed with ethanol. The combined filtrates were evaporated to dryness to yield oily [1$\alpha$,3$\beta$]-1,3-bis[(tetrahydro-2H-pyran-2-yl)oxy]pregn-5-en-21-oic acid ethyl ester, [$\alpha$]$_D^{23}$−13° (c 1, CHCl$_3$).

EXAMPLE 13

To a solution of 1.0 mL of diisopropylamine in 3 mL of tetrahydrofuran at −30° C. was added 3.82 mL (0.0061 mol) of 1.6 M of butyllithium in hexane. After stirring for 0.5 hr, 3.03 g (0.0056 mol) of [1$\alpha$,3$\beta$]-1,3-bis[(tetrahydro-2H-pyran-2-yl)oxy]pregn-5-en-21-oic acid ethyl ester in 30 mL of tetrahydrofuran was added dropwise to yield the lithium enolate of [1$\alpha$,3$\beta$]-1,3-bis[-tetrahydro-2H-pyran-2-yl)oxy]pregn-5-en-21-oic acid ethyl ester. The mixture was stirred for 1 hr at −30° C. and cooled to −70° C. A solution of 2.30 g (0.0068 mol) of 4-(1-ethoxyethoxy)-3,3-difluoro-1-iodo-4-methylpentane in 5 mL of hexamethylphosphoramide was added dropwise. The mixture was stirred at −70° C. for 1 hr and was allowed to warm to 25° C. and stir for 1 hr. The mixture was then diluted with 9:1 hexane-ether. The solution was washed with water, and saturated brine. The organic phase was dried over anhydrous magnesium sulfate, filtered, and evaporated to dryness. The residue was purified by column chromatography on 0.06–0.20 mm silica gel to give [1$\alpha$,3$\beta$]-1,3-bis[(tetrahydro-2H-yran-2-yl)oxy]-25-(1-ethoxyethoxy)-24,24-difluorocholest-5-en-21-oic acid ethyl ester, [$\alpha$]$_D^{20}$+10° (c 1, CHCl$_3$).

EXAMPLE 14

To a mixture of 0.20 g (0.0053 mol) of lithium aluminum hydride and 10 mL of tetrahydrofuran at 0° C. was added 2.55 g (0.0034 mol) of [1$\alpha$,3$\beta$]-1,3-bis[tetrahydro-2H-pyran-2-yl)oxy]-25-(1-ethoxyethoxy)-24,24-difluorocholest-5-en-21-oic acid ethyl ester in 35 mL of tetrahydrofuran. The mixture was heated at 50° C. for 1.5 hr, recooled to 0° C., and diluted with 120 mL of ether. The mixture was then quenched with the dropwise addition of 0.40 ml of water and 0.32 mL of 10% aqueous sodium hydroxide. The mixture was stirred at 25° C. for 1 hr and was filtered. The solids were triturated with ether and filtered. Evaporation of solvent afforded [1α,3β]-1,3-bis[tetrahydro-2H-pyran-2-yl)oxy]-25-(1-ethoxyethoxy)-24,24-difluorocholest-5-en-21ol, [α]$_D^{20}$+4° (c 1, CHCl$_3$).

EXAMPLE 15

A mixture of 2.37 g (0.0033 mol) of [1α,3β]-1,3-bis[-(tetrahydro-2H-pyran-2-yl)oxy]-25-(1-ethoxyethoxy)-24,24-difluorocholest-5-en-21-ol, 7 mL of pyridine and 1.27 g (0.0067 mol) of p-toluenesulfonyl chloride was stirred at 0° C. for 18 hr. The mixture was quenched with ice chips. The mixture was then poured into water and extracted with methylene chloride. The organic phase was washed with 10% aqueous sulfuric acid and saturated aqueous sodium bicarbonate solution. The organic layer was dried over anhydrous magnesium sulfate, filtered and evaporated to dryness to yield oily [1α,3β]-1,3-bis[(tetrahydro-2H-pyran-2-yl)oxy]-25-(1-ethoxyethoxy)-24,24-difluorocholest-5-en-21-ol 21-(4-methylbenzenesulfonate), [α]$_D^{20}$+6° (c 1, CHCl$_3$).

EXAMPLE 16

A mixture of 0.221 g (0.00025 mol) of [1α,3β]-1,3-bis[(tetrahydro-2H-pyran-2-yl)oxy]-25-(1-ethoxyethoxy)-24,24-difluorocholest-5-en-21-ol 21-(4-methylbenzenesulfonate), and 0.150 g (0.0010 mol) of sodium iodide in 2 mL of acetone was heated at 50° for 18 hr and cooled. The mixture was poured into water and the product was isolated with methylene chloride. The organic layers were washed with aqueous sodium sulfite solution, and saturated aqueous sodium bicarbonate solution. The organic layers were dried over anhydrous magnesium sulfate, filtered and evaporated to dryness to yield [1α,3β]-bis[(tetrahydro-2H-pyran-2-yl)oxy]-25-(1-ethoxyethoxy)-24,24-difluoro-21-iodocholest-5-ene.

EXAMPLE 17

A. A mixture of 0.410 g (0.0108 mol) of lithium aluminum hydride, 50 mL of tetrahydrofuran and 2.98 g (0.0033 mol) of [1α,3β]-1,3-bis[(tetrahydro-2H-pyran-2-yl)oxy]-25-(1-ethoxyethoxy)-24,24-difluorocholest-5-en-21-ol 21-(4-methylbenzenesulfonate) was heated at reflux (60°) for 1 hr and cooled to 0° C. The mixture was diluted with 120 mL of ether and quenched with the dropwise addition of 0.82 mL of water and 0.65 mL of 10% aqueous sodium hydroxide solution. The mixture was then dried for 1 hr and filtered. The solids were triturated with ether and filtered. The combined filtrates were evaporated to dryness and chromatographed on 0.06–0.20 mm silica gel to yield [1α,3β]-1,3-bis[(tetrahydro-2H-pyran-2-yl)oxy]-25-(1-ethoxyethoxy)-24,24-difluorocholest-5-ene, [α]$_D^{16}$+2° (c 1, CHCl$_3$).

B. By an alternative procedure, a mixture of 0.205 g (0.00025 mol) of [1α,3β]-1,3-bis[(tetrahydro-2H-pyran-2-yl)oxy]-25-(1-ethoxyethoxy)-24,24-difluoro-21-iodocholest-5-ene, 0.987 g (0.00030 mol) of tri-n-butyltin hydride and 3 mL of tetrahydrofuran were stirred at 25° C. for 18 hr under an argon atmosphere. The mixture was evaporated to dryness and the residue was purified by chromatography on 0.06–0.20 mm silica gel to yield [1α,3β]-1,3-bis[(tetrahydro-2H-pyran-2-yl)oxy]-25-(1-ethoxyethoxy)-24,24-difluorocholest-5-ene, [α]$_D^{18}$+2° (c 1, CHCl$_3$).

EXAMPLE 18

A mixture of 1.87 g (0.0027 mol) of [1α,3β]-1,3-bis[-(tetrahydro-2H-pyran-2-yl)oxy]-25-(1-ethoxyethoxy)-24,24-difluorocholest-5-ene, 70 mL of methanol and 0.30 g of p-toluenesulfonic acid monohydrate was stirred at 25° C. for 4 hr. The mixture was quenched by adding 1.0 g of sodium bicarbonate and stirring for 0.5 hr. The mixture was then evaporated to dryness. The residue was triturated with ethyl acetate, filtered, and evaporated to dryness. The crude solid was recrystallized from ethyl acetate to yield [1α,3β]-24,24-difluorocholest-5-en-1,3,25-triol, mp 177°–179°, [α]$_D^{21}$−15° (c 0.6, MeOH).

EXAMPLE 19

A mixture of 0.86 g (0.0019 mol) of [1α,3β]-24,24-difluorocholest-5-en-1,3,25-triol, 7 mL of pyridine and 4 mL of acetic anhydride were stirred at 0° C. for 1 hr and at 25° C. for 30 hr. The mixture was diluted with 20 mL of methanol at 0° C. and evaporated to dryness. The residue was then dissolved in methylene chloride. This solution was washed with 10% aqueous sulfuric acid and saturated sodium bicarbonate solution. The organic phase was dried over anhydrous magnesium sulfate, filtered, and evaporated to dryness to yield [1α,3β]-24,24-difluorocholest-5-en-1,3,25-triol, 1,3-diacetate, [α]$_D^{22}$−20° (c 1, CHCl$_3$).

EXAMPLE 20

A mixture of 1.05 g (0.0019 mol) of [1α,3β]-24,24-difluorocholest-5-en-1,3,25-triol 1,3-diacetate, 0.84 g of sodium bicarbonate, 0.357 g (0.0012 mol) of 1,3-dibromo-5,5-dimethylhydrantoin and 40 mL of hexane was heated at reflux (80° C.) for 1 hour and cooled. The mixture was filtered and the solids were triturated with hexane and filtered. The filtrates were evaporated to dryness to yield [1α,3β,7ξ]-7-bromo-24,24-difluorocholest-5-en-1,3,25-triol 1,3-diacetate.

EXAMPLE 21

A mixture of 1.33 g (0.0019 mol) of [1α,3β,7ξ]-7-bromo-24,24-difluorocholest-5-en-1,3,25-triol 1,3-diacetate, 0.8 mL of s-collidine and 10 mL of xylene was heated at reflux (140° C.) for 0.5 hr and cooled. The mixture was diluted with 30 mL of benzene. This solution was washed with 10% aqueous sulfuric acid, and saturated aqueous sodium bicarbonate solution. The organic phase was dried over anhydrous magnesium sulfate, filtered, and evaporated to dryness. The residue was purified by column chromatography on 0.06–0.20 mm silica gel to yield [1α,3β]-24,24-difluorocholesta-5,7-dien-1,3,25-triol 1,3-diacetate, [α]$_D^{25}$−31° (c 0.4, CHCl$_3$), mp 130°–132°. UV max (C$_2$H$_5$OH) 261 (ε7750), 270 (ε11,200), 281 (ε12,100) and 293 nm (ε7100).

EXAMPLE 22

A mixture of 0.210 g (0.0004 ml) of [1α,3β]-24,24-difluorocholesta-5,7-dien-1,3,25-triol 1,3-diacetate in 40 mL of hexane and 10 mL of tetrahydrofuran was irradiated for 0.5 hr under argon at −5° C. using a 450 W Hanovia high pressure mercury lamp, cooled with a Vycor-glass cooling finger. The solution was evaporated to dryness and the residue was purified with a Waters Associates Liquid chromatograph Model 202 using 4'×1" silica gel column and a 3:1 mixture of n-hexane-ethyl acetate as eluant to give [1α,3β,6Z]-24,24- difluoro-9,10-secocholest-5(10),6,8-trien-1,3,25-triol 1,3-diacetate. UV max (C$_2$H$_5$OH) 260 nm ($\epsilon$10,700).

EXAMPLE 23

A solution of 0.071 g (0.00013 mol) of [1α,3β,6Z]-24,24-difluoro-9,10-secocholesta-5(10),6,8-trien-1,3,25-triol 1,3-diacetate, and 7 mL of 1.5% potassium hydroxide in methanol was stirred at 0° C. for 4 hr. The mixture was neutralized to pH 7.5 with glacial acetic acid in methanol. The solution was then evaporated to dryness at 0° C. The residue was partitioned between ethyl acetate and water. The organic phase was washed with saturated brine and dried over anhydrous sodium sulfate. The mixture was filtered and evaporated to dryness to yield [1α,3β,6Z]-24,24-difluoro-9,10-secocholesta-5(10),6,8-trien-1,3,25-triol. UV max (C$_2$H$_5$OH) 260 nm ($\epsilon$10,800). The reaction was carried out under an argon atmosphere.

EXAMPLE 24

A mixture of 0.063 g (0.00013 mol) of [1α,3β,6Z]-24,24-difluoro-9,10-secocholesta-5(10),6,8-trien-1,3,25-triol, and 10 mL of p-dioxane was heated at reflux (100° C.) for 1 hr and cooled. The mixture was then evaporated to dryness. The residue was purified with a Waters Associates liquid chromatograph Model 202 using a 4'×1" silica gel column and 3:1 ethyl acetatehexane as eluant to give [1α,3β,5Z,7E]-24,24-difluoro-9,10-secocholesta-5,7,10(19)-trien-1,3,25-triol also known as 24,24-difluoro-1α,25-dihydroxycholecalciferol, $[\alpha]_D^{21}$+49° (c 0.5, MeOH). UV max (C$_2$H$_5$OH) 265 nm ($\epsilon$15,500).

EXAMPLE 25

In a manner analogous to example 24, when [1α,3β,6Z]-24,24-difluoro-9,10-secocholesta-5(10),6,8-trien-1,3,25-triol 1,3-diacetate is heated in p-dioxane at reflux (100° C.), [1α,3β,5Z,7E]-24,24-difluoro-9,10-secocholesta-5,7,10(19)-trien-1,3,25-triol 1,3-diacetate can be obtained.

EXAMPLE 26

In a manner analogous to example 23, when [1α,3β,5Z,7E]-24,24-difluoro-9,10-secocholesta-5,7,10(19)-trien-1,3,25-triol 1,3-diacetate is reacted with 1.5% potassium hydroxide in methanol, [1α,3β,5Z,7E]-24,24-difluoro-9,10-secocholesta-5,7,10(19)-trien-1,3,25-triol also known as 24,24-difluoro-1α,25-dihydroxycholecalciferol can be obtained.

EXAMPLE 27

In a manner analogous to example 2, when 2,2-difluorosuccinic anhydride is reacted with benzyl alcohol, benzyl 2,2-difluoro-3-carboxypropionate can be obtained.

EXAMPLE 28

In a manner analogous to example 2, when 2,2-difluorosuccinic anhydride is reacted with phenol, phenyl 2,2-difluoro-3-carboxypropionate can be obtained.

EXAMPLE 29

In a manner analogous to example 3, when benzyl 2,2-difluoro-3-carboxypropionate is reacted with borane in tetrahydrofuran, benzyl 2,2-difluoro-4-hydroxybutyrate can be obtained.

EXAMPLE 30

In a manner analogous to example 3, when phenyl 2,2-difluoro-3-carboxypropionate is reacted with borane in tetrahydrofuran, phenyl 2,2-difluoro-4-hydroxybutyrate can be obtained.

EXAMPLE 31

In a manner analogous to example 4, when benzyl 2,2-difluoro-4-hydroxybutyrate is reacted with ethereal methyllithium, 4-methyl-3,3-difluoro-1,4-pentanediol can be obtained.

EXAMPLE 32

In a manner analogous to example 5, when 4-methyl-3,3-difluoro-1,4-pentanediol, is reacted with pyridine and benzoyl chloride, 4-methyl-3,3-difluoro-1,4-pentanediol 1-benzoate can be obtained.

EXAMPLE 33

In a manner analogous to example 6, when 4-methyl-3,3-difluoro-1,4-pentanediol 1-benzoate is reacted with ethyl vinyl ether and p-toluenesulfonic acid monohydrate, 4-(1-ethoxyethoxy)-3,3-difluoro-4-methyl-1-pentanol 1-benzoate can be obtained.

EXAMPLE 34

In a manner analogous to example 6, when 4-methyl-3,3-difluoro-1,4-pentanediol 1-acetate is reacted with 3,4-dihydro-2H-pyran and p-toluenesulfonic acid monohydrate, 4-[(tetrahydro-2H-pyran-2-yl)oxy]-3,3-difluoro-4-methyl-1-pentanol 1-acetate can be obtained.

EXAMPLE 35

In a manner analogous to example 7, when lithium aluminum hydride is reacted with 4-(1-ethoxyethoxy)-3,3-difluoro-4-methyl-1-pentanol 1-benzoate, 4-(1-ethoxyethoxy)-3,3-difluoro-4-methyl-1-pentanol can be obtained.

EXAMPLE 36

In a manner analogous to example 8, when 4-(1-ethoxyethoxy)-3,3-difluoro-4-methyl-1-pentanol is reacted with pyridine and methanesulfonyl chloride, 4-(1-ethoxyethoxy)-3,3-difluoro-4-methyl-1-pentanol 1-methanesulfonate can be obtained.

EXAMPLE 37

In a manner analogous to example 9, when 4-(1-ethoxyethoxy)-3,3-difluoro-4-methyl-1-pentanol 1-methanesulfonate is reacted with sodium bromide, 4-(1-ethoxyethoxy)-3,3-difluoro-1-bromo-4-methylpentane can be obtained.

EXAMPLE 38

In a manner analogous to example 9, when 4-(1-ethoxyethoxy)-3,3-difluoro-4-methyl-1-pentanol 1-methanesulfonate is reacted with sodium iodide, 4-(1-ethoxyethoxy)-3,3-difluoro-1-iodo-4-methylpentane can be obtained.

EXAMPLE 39

When a mixture of [1α,3β]-1,3-dihydroxyandrost-5-en-17-one, pyridine and benzyl bromide is reacted, [1α3β]-1,3-dibenzyloxyandrost-5-en-17-one can be obtained.

EXAMPLE 40

When a mixture of [1α,3β]-1,3-dihydroxyandrost-5-en-17-one, dimethylformamide, imidazole, and t-butyldimethylchlorosilane is reacted, [1α,3β]-1,3-bis(t-butyldimethylsilyloxy)-androst-5-en-17-one can be obtained.

EXAMPLE 41

In a manner analogous to example 11, when [1α,3β]-1,3-dibenzyloxyandrost-5-en-17-one is reacted with triethyl phosphonoacetate and ethanolic sodium ethoxide, [1α,3β,17(20)E]-1,3-dibenzyloxypregn-5,17(20)-dien-21-oic acid ethyl ester can be obtained.

EXAMPLE 42

In a manner analogous to example 11, when [1α,3β]-1,3-bis(t-butyldimethylsilyloxy)androst-5-en-17-one is reacted with triethyl phosphonoacetate and ethanolic sodium ethoxide, [1α,3β,17(20)E]-1,3-bis(t-butyldimethylsilyloxy)pregn-5,17(20)-dien-21-oic acid ethyl ester can be obtained.

EXAMPLE 43

In a manner analogous to example 12, when [1α,3β,17(20)E]-1,3-dibenzyloxypregn-5,17(20)-dien-21-oic acid ethyl ester is reacted with platinum oxide catalyst and hydrogen, [1α,3β]-1,3-dibenzyloxypregn-5-en-21-oic acid ethyl ester can be obtained.

EXAMPLE 44

In a manner analogous to example 12, when [1α,3β,17(20)E]-1,3-bis(t-butyldimethylsilyloxy)pregn-5,17(20)-dien-21-oic acid ethyl ester is reacted with platinum oxide catalyst and hydrogen, [1α,3β]-1,3-bis(t-butyldimethylsilyloxy)pregn-5-en-21-oic acid ethyl ester can be obtained.

EXAMPLE 45

In a manner analogous to example 13, when [1α,3β]-1,3-dibenzyloxypregn-5-en-21-oic acid ethyl ester is reacted with lithium diisopropylamide and 4-(1-ethoxyethoxy)-3,3-difluoro-1-iodo-4-methylpentane, [1α,3β]-1,3-dibenzyloxy-25-(1-ethoxyethoxy)-24,24-difluorocholest-5en-21-oic acid ethyl ester can be obtained.

EXAMPLE 46

In the manner analogous to example 13, when [1α,3β]-1,3-bis(t-butyldimethylsilyloxy)pregn-5-en-21-oic acid ethyl ester is reacted with lithium diisopropylamide and 4-(1-ethoxyethoxy)-3,3-difluoro-1-iodo-4-methylpentane, [1α,3β]-1,3-bis(t-butyldimethylsilyloxy)-25-(1-ethoxyethoxy)-24,24-difluorocholest-5-en-21-oic acid ethyl ester can be obtained.

EXAMPLE 47

In a manner analogous to example 14, when [1α,3β]-1,3-dibenzyloxy-25-(1-ethoxyethoxy)-24,24-difluorocholest-5-en-21-oic acid ethyl ester is reacted with lithium aluminum hydride, [1α,3β]-1,3-dibenzyloxy-25-(1-ethoxyethoxy)-24,24-difluorocholest-5-en-21-ol can be obtained.

EXAMPLE 48

In a manner analogous to example 14, when [1α,3β]-1,3-bis(t-butyldimethylsilyloxy)-25-(1-ethoxyethoxy)-24,24-difluorocholest-5-en-21-oic acid ethyl ester is reacted with lithium aluminum hydride, [1α,3β]-1,3-bis(t-butyldimethylsilyloxy)-25-(1-ethoxyethoxy)-24,24-difluorocholest-5-en-21-ol can be obtained.

EXAMPLE 49

In a manner analogous to example 15, when [1α,3β]-1,3-dibenzyloxy-25-(1-ethoxyethoxy)-24,24-difluorocholest-5-en-21-ol is reacted with pyridine and p-toluenesulfonyl chloride, [1α,3β]-1,3-dibenzyloxy-25-(1-ethoxyethoxy)-24,24-difluorocholest-5-en-21-ol 21-(4-methylbenzenesulfonate) can be obtained.

EXAMPLE 50

In a manner analogous to example 15, when [1α,3β]-1,3-bis(t-butyldimethylsilyloxy)-25-(1-ethoxyethoxy)-24,24-difluorocholest-5-en-21-ol is reacted with pyridine and p-toluenesulfonyl chloride, [1α,3β]-1,3-bis(t-butyldimethylsilyloxy)-25-(1-ethoxyethoxy)-24,24-difluorocholest-5-en-21-ol 21-(4-methylbenzenesulfonate) can be obtained.

EXAMPLE 51

In a manner analogous to example 17A, when [1α,3β]-1,3-dibenzyloxy-25-(1-ethoxyethoxy)-24,24-difluorocholest-5-en-21-ol 21-(4-methylbenzenesulfonate) is reacted with lithium aluminum hydride, [1α,3β]-1,3-dibenzyloxy-25-(1-ethoxyethoxy)-24,24-difluorocholest-5-ene can be obtained.

EXAMPLE 52

In a manner analogous to example 17A, when [1α,3β]-1,3-bis(t-butyldimethylsilyloxy)-25-(1-ethoxyethoxy)-24,24-difluorocholest-5-en-21-ol 21-(4-methylbenzenesulfonate) is reacted with lithium aluminum hydride, [1α,3β]-1,3-bis(t-butyldimethylsilyloxy)-25-(1-ethoxyethoxy)-24,24-difluorocholest-5-ene can be obtained.

EXAMPLE 53

When a mixture of [1α,3β]-1,3-dibenzyloxy-25-(1-ethoxyethoxy)-24,24-difluorocholest-5-ene in methylene chloride was treated with trimethylsilyl iodide [1α,3β]-24,24-difluorocholest-5-en-1,3,25-triol also known as 24,24-difluoro-1α,25-dihydroxycholesterol can be obtained.

EXAMPLE 54

When a mixture of [1α,3β]-1,3-bis(t-butyldimethylsilyloxy)-25-(1-ethoxyethoxy)-24,24-difluorocholest-5-ene, in methanol is reacted with p-toluenesulfonic acid monohydrate, [1α,3β]-24,24-difluorocholest-5-en-1,3,25-triol also known as 24,24-difluoro-1α,25-dihydroxycholesterol can be obtained.

EXAMPLE 55

When a mixture of [1α,3β]-24,24-difluorocholest-5-en-1,3,25-triol in pyridine is reacted with acetic anhydride and a catalytic amount of 4-dimethylaminopyridine, [1α,3β]-24,24-difluorocholest-5-en-1,3,25-triol 1,3,25-triacetate can be obtained.

EXAMPLE 56

In the same manner as example 20, when [1α,3β]-1,3-bis[(tetrahydro-2H-pyran-2-yl)oxy]-25-(1-ethoxyethoxy)-24,24-difluorocholest-5-ene is reacted with 1,3-dibromo-5,5-dimethylhydantoin, and sodium bicarbonate, [1α,3β7ξ]-1,3-bis[(tetrahydro-2H-pyran-2-yl)oxy]-7-bromo-25-(1-ethoxyethoxy)-24,24-difluorocholest-5-ene can be obtained.

EXAMPLE 57

In the same manner as example 20, when [1α,3β]-1,3-dibenzyloxy-25-(1-ethoxyethoxy)-24,24-difluorocholest-5-ene is reacted with 1,3-dibromo-5,5-dimethylhydrantoin, and sodium bicarbonate [1α,3β7ξ]-7-bromo-1,3-dibenzyloxy-25-(1-ethoxyethoxy)-24,24-difluorocholest-5-ene can be obtained.

EXAMPLE 58

In the same manner as example 20, when [1α,3β]-1,3-bis(t-butyldimethylsilyloxy)-25-(1-ethoxyethoxy)-24,24-difluorocholest-ene is reacted with 1,3-dibromo-5,5-dimethylhydantoin and sodium bicarbonate, [1α,3β,7ξ]-1,3-bis(t-butyldimethylsilyloxy)-7-bromo-25-(1-ethoxyethoxy)-24,24-difluorocholest-5-ene can be obtained.

EXAMPLE 59

In the same manner as example 20, when [1α,3β]-24,24-difluorocholest-5-en-1,3,25-triol, 1,3,25-triacetate is reacted with 1,3-dibromo-5,5-dimethylhydantoin and sodium bicarbonate, [1α,3β,7ξ]-7-bromo-24,24-difluorocholest-5-en-1,3,25-triol 1,3,25-triacetate can be obtained.

EXAMPLE 60

In the same manner as example 21, when [1α,3β,7ξ]-1,3-bis[(tetrahydro-2H-pyran-2-yl)oxy]-7-bromo-25-(1-ethoxyethoxy)-24,24-difluorocholest-5-ene is reacted with s-collidine and xylene, [1α,3β]-1,3-bis[(tetrahydro-2H-pyran-2-yl)oxy]-25-(1-ethoxyethoxy)-24,24-difluorocholesta-5,7-diene can be obtained.

EXAMPLE 61

In the same manner as example 21, when [1α,3β,7ξ]-7-bromo-1,3-dibenzyloxy-25-(1-ethoxyethoxy)-24,24-difluorocholest-5-ene is reacted with s-collidine and xylene, [1α,3β]-1,3-dibenzyloxy-25-(1-ethoxyethoxy)-24,24-difluorocholesta-5,7-diene can be obtained.

EXAMPLE 62

In the same manner as example 21, when [1α,3β,7ξ]-1,3-bis(t-butyldimethylsilyloxy)-7-bromo-25-(1-ethoxyethoxy)-24,124-difluorocholest-5-ene is reacted with s-collidine and xylene, [1α,3β]-1,3-bis(t-butyldimethylsilyloxy)-25-(1-ethoxyethoxy)-24,24-difluorocholesta-5,7-diene can be obtained.

EXAMPLE 63

In the same manner as example 21, when [1α,3β,7ξ]-7-bromo-24,24-difluorocholest-5-en-1,3,25-triol 1,3,25-triacetate is reacted with s-collidine and xylene, [1α,3β]-24,24-difluorocholesta-5,7-diene-1,3,25-triol 1,3,25-triacetate can be obtained.

EXAMPLE 64

In the same manner as example 22, when [1α,3β]-1,3-bis[(tetrahydro-2H-pyran-2-yl)oxy]-25-(1-ethoxyethoxy)-24,24-difluorocholesta-5,7-diene is irradiated under argon, [1α,3β,6Z]-1,3-bis[(tetrahydro-2H-pyran-2-yl)oxy]-25-(1-ethoxyethoxy)-24,24-difluoro-9,10-secocholesta-5(10),6,8-triene can be obtained.

EXAMPLE 65

In the same manner as example 22, when [1α,3β]-1,3-dibenzyloxy-25-(1-ethoxyethoxy)-24,24-difluorocholesta-5,7-diene, is irradiated under argon [1α,3β,6Z]-1,3-dibenzyloxy-25-(1-ethoxyethoxy)-24,24-difluoro-9,10-secocholesta-5(10),6,8-triene can be obtained.

EXAMPLE 66

In a manner analogous to example 22, when [1α,3β]-1,3-bis(t-butyldimethylsilyloxy)-25-(1-ethoxyethoxy)-24,24-difluorocholesta-5,7-diene, is irradiated under argon, [1α,3β,6Z]-1,3-dibenzyloxy-25-(1-ethoxyethoxy)-24,24-difluoro-9,10-secocholesta-5(10),6,8-triene can be obtained.

EXAMPLE 67

In a manner analogous to example 22, when [1α,3β]-24,24-difluorocholesta-5,7-dien-1,3,25-triol 1,3,25-triacetate, is irradiated under argon, [1α,3β,6Z]-24,24-difluoro-9,10-secocholesta-5(10),6,8-trien-1,3,25-triol 1,3,25-triacetate can be obtained.

EXAMPLE 68

In the same manner as example 24, when [1α,3β,6Z]-1,3-bis[(tetrahydro-2H-pyran-2-yl)oxy]-25-(1-ethoxyethoxy)-24,24-difluoro-9,10-secocholesta-5(10),6,8-triene is heated in p-dioxane at 100° C. under argon, [1α,3β,5Z,7E]-1,3-bis[(tetrahydro-2H-pyran-2-yl)oxy]-25-(1-ethoxyethoxy)-24,24-difluoro-9,10-secocholesta-5,7,10(19)-triene can be obtained.

EXAMPLE 69

In the same manner as example 24, when [1α,3β,6Z]-1,3-dibenzyloxy-25-(1-ethoxyethoxy)-24,24-difluoro-9,10-secocholesta-5(10),6,8-triene is heated in p-dioxane at 100° C. under argon, [1α,3β,5Z,7E]-1,3-dibenzyloxy-25-(1-ethoxyethoxy)-24,24-difluoro-9,10-secocholesta-5,7,10(19)-triene can be obtained.

EXAMPLE 70

In the same manner as example 24, when [1α,3β,6Z]-1,3-bis(t-butyldimethylsilyloxy)-25-(1-ethoxyethoxy)-24,24-difluoro-9,10-secocholesta-5(10),6,8-triene is heated in p-dioxane at 100° C. under argon, [1α,3β,5Z,7E]-1,3-bis(t-butyldimethylsilyloxy)-25-(1-ethoxyethoxy)-b 24,24-difluoro-9,10-secocholesta-5,7,10(19)-triene can be obtained.

EXAMPLE 71

In the same manner as example 24, when [1α,3β,6Z]-24,24-difluoro-9,10-secocholesta-5(10),6,8-trien-1,3,25-triol 1,3,25-triacetate is heated in p-dioxane at 100° C. under argon, [1α,3β,5Z,7E]-24,24-difluoro-9,10-secocholesta-5,7,10(19)-trien-1,3,25-triol 1,3,25-triacetate can be obtained.

EXAMPLE 72

When [1α,3β,5Z,7E]-1,3-bis[(tetrahydro-2H-pyran-2-yl)oxy]-25-(1-ethoxyethoxy)-24,24-difluoro-9,10-secocholesta-5,7,10(19)-triene is reacted with the hydrogen form of a cation exchange resin (Bio-Rad A G 50W-X4) in methanol, 24,24-difluoro-1α,25-dihydroxycholecalciferol can be obtained.

EXAMPLE 73

When [1α,3β,5Z,7E]-1,3-dibenzyloxy-25-(1-ethoxyethoxy)-24,24-difluoro-9,10-secocholesta-5,7,10(19)-triene is reacted with trimethylsilyl iodide, 24,24-difluoro-1α, 25-dihyroxycholecalciferol can be obtained.

EXAMPLE 74

In the same manner as example 72, when [1α,3β,5Z,7E]-1,3-bis(t-butyldimethylsilyloxy)-25-(1-ethoxyethoxy)-24,24-difluoro-9,10-secocholesta-5,7,10(19)-triene is reacted with the hydrogen form of a cation exchange resin (Bio-Rad AG 50W-X4), and methanol, 24,24-difluoro-1α,25-dihydroxycholecalciferol can be obtained.

EXAMPLE 75

In the same manner as example 23, when [1α,3β,5Z,7E]-24,24-difluoro-9,10-secocholesta-5,7,10(19)-trien-1,3,25-triol 1,3,25-triacetate is reacted with 1.5% potassium hydroxide in methanol, 24,24-difluoro-1α,25-dihydroxycholecalciferol can be obtained.

EXAMPLE 76

| Item | Ingredients | mg/capsule | | |
|---|---|---|---|---|
| 1. | 24,24-difluoro-1α,25-dihydroxycholecalciferol | 0.00005 | 0.0001 | 0.0002 |
| 2. | polyethylene glycol 400 (PEG 400) | 200.00000 | 200.0000 | 200.0000 |
| 3. | butylated hydroxy anisole (BHA) | 0.10000 | 0.1000 | 0.1000 |
| 4. | ascorbyl palmitate | 1.00000 | 1.0000 | 1.0000 |

Procedure:

Dissolve items 1, 3 and 4 in item 2, under a blanket of nitrogen and encapsulate.

What is claimed is:

1. A process for the preparation of a compound of the formula

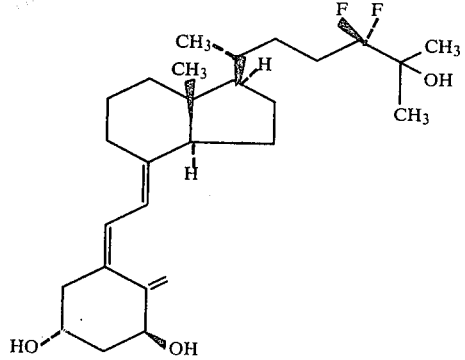

I which process comprises reacting a compound of the formula

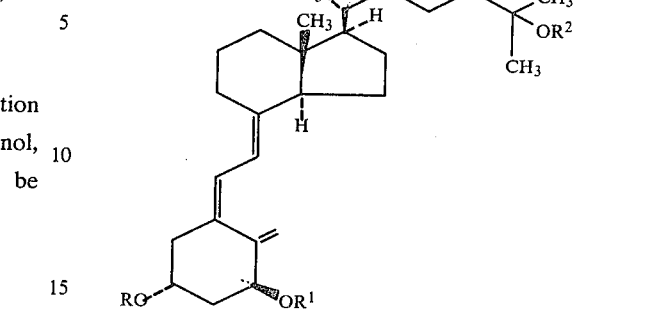

II wherein F is fluorine, and R, $R^1$ and $R^2$ are lower alkyl, aralkyl, aryl, tri-lower alkylsilyl, di-lower alkylarylsilyl, lower-alkyldiarylsilyl, triarylsilyl or a group of the formula

III wherein $R^3$ is hydrogen or lower alkyl; $R^4$ and $R^5$ each independently is lower alkyl and $R^4$ and $R^5$ each taken together are lower alkylene of from 3 to 6 carbon atoms,
with acid in a protic solvent at temperatures in the range of about $-10°$ C. to about 80° C.

2. The process according to claim 1 wherein said protic solvent is methanol.

3. The process according to claim 1 wherein said acid is a cationic exchange resin in the hydrogen form.

4. The process according to claim 1 wherein said reaction is carried out at temperatures in the range of about 0° C. to about 40° C.

5. A process for the synthesis of a compound of the formula

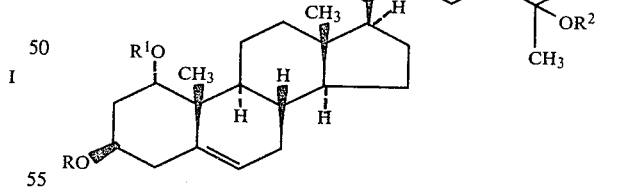

VIII wherein F is fluorine, R and $R^1$ are lower alkyl, aralkyl, aryl, tri-lower alkylsilyl, di-lower alkylarylsilyl, lower-alkyldiarylsilyl, triarylsilyl or a group of the formula

III wherein $R^3$ is hydrogen or lower alkyl; $R^4$ and $R^5$ each independently is lower alkyl and $R^4$ and $R^5$ taken together are lower alkylene of from 3 to 6 carbon atoms which process comprises the steps of;
(a) reacting a compound of the formula

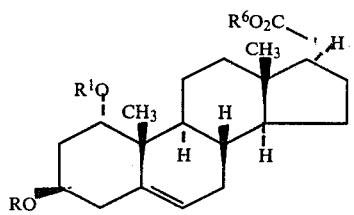   V wherein R and R¹ are lower alkyl, aralkyl, aryl, tri-lower alkylsilyl, di-lower alkylarylsilyl, lower-alkyldiarylsilyl, triarylsilyl or a group of the formula

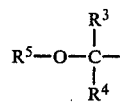   III wherein R³ is hydrogen or lower alkyl; R⁴ and R⁵ each independently is lower alkyl and R⁴ and R⁵ taken together are lower alkylene of from 3 to 6 carbon atoms and R⁶ is lower alkyl, aralkyl or aryl with an organometallic reagent in an aprotic solvent at temperatures in the range of from about −78° C. to about 0° C. so as to yield a compound of the formula

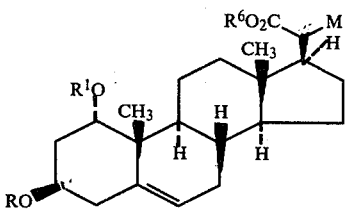   VI wherein R, R¹ and R⁶ are as above and M is lithium, sodium, potassium, magnesium/2 or zinc/2

(b) reacting the reaction product of step (a) with a compound of the formula

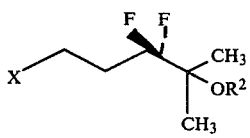   VII wherein X is iodo, bromo, chloro, lower alkylsulfonyloxy, phenylsulfonyloxy, or substituted phenylsulfonyloxy; F is fluorine and R² is lower alkyl, aralkyl, aryl, tri-lower alkylsilyl, di-lower alkylarylsilyl, lower-alkyldiarylsilyl, triarylsilyl or a group of the formula

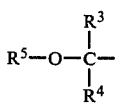   III wherein R³ is hydrogen or lower alkyl; R⁴ and R⁵ each independently is lower alkyl and R⁴ and R⁵ taken together are lower alkylene of from 3 to 6 carbon atoms in an aprotic solvent at temperatures in the range of from about −78° C. to about 60° C. so as to yield the compound of the formula

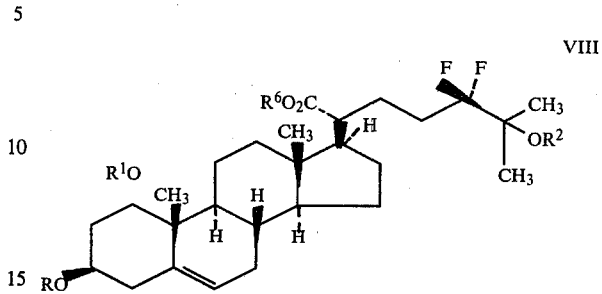   VIII wherein F, R, R¹ and R⁴ are as above.

6. The process according to claim 5 wherein said organometallic reagent is lithium diisopropylamide.

7. The process according to claim 5 wherein X is iodo.

8. The process according to claim 5 wherein said reaction is carried out at temperatures in the range of from about −40° C. to about 0° C.

9. The process according to claim 5 wherein said aprotic inert solvent is a mixture of tetrahydrofuran and hexamethylphosphoramide.

10. A process for the preparation of a compound of the formula

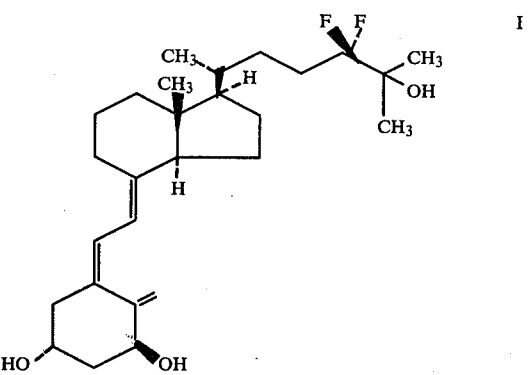   I which process comprises the steps of
(a) thermally rearranging a compound of the formula

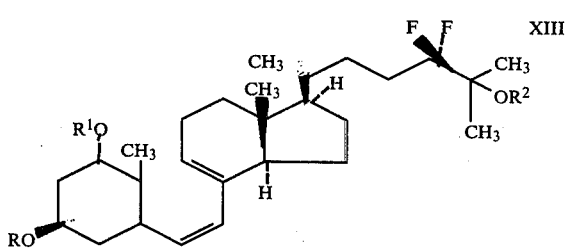   XIII wherein F is fluorine, and R, R¹ and R² are lower alkyl, aralkyl, aryl, tri-lower alkylsilyl, di-lower alkylarylsilyl, lower-alkyldiarylsilyl, triarylsilyl or a group of the formula $$R^5-O-\underset{\underset{R^4}{|}}{\overset{\overset{R^3}{|}}{C}}- \quad \text{III}$$

wherein $R^3$ is hydrogen or lower alkyl; $R^4$ and $R^5$ each independently are lower alkyl and $R^4$ and $R^5$ each taken together are lower alkylene of from 3 to 6 carbon atoms at temperatures in the range of from about 50° C. to about 100° C. in an inert solvent under an inert atmosphere;

(b) reacting the reaction product step (a) with acid in a protic solvent at temperatures in the range of from about −10° C. to about 80° C.

11. The process according to claim 10 steb (b) wherein said acid is a cationic exchange resin in the hydrogen form.

12. The process according to claim 10 steb (b) wherein said temperature is in the range of from about 0° C. to about 40° C.

13. The process according to claim 10 steb (b) wherein said protic solvent is methanol.

14. A compound of the formula

[Structure II]

wherein F is fluorine and R, $R^1$ and $R^2$ are tri-lower alkylsilyl, di-lower alkylarylsilyl, lower-alkyldiarylsilyl, triarylsilyl or a group of the formula $$R^5-O-\underset{\underset{R^4}{|}}{\overset{\overset{R^3}{|}}{C}}- \quad \text{III}$$

wherein $R^3$ is hydrogen or lower alkyl; $R^4$ and $R^5$ each independently are lower alkyl and $R^4$ and $R^5$ taken together are lower alkylene of from 3 to 6 carbon atoms.

15. The compound according to claim 14 wherein R, $R^1$ and $R^2$ are a group of the formula $$R^5-O-\underset{\underset{R^4}{|}}{\overset{\overset{R^3}{|}}{C}}- \quad \text{III}$$

wherein $R^3$ is hydrogen or lower alkyl; $R^4$ and $R^5$ each independently are lower alkyl and $R^4$ and $R^5$ taken together are lower alkylene of from 3 to 6 carbon atoms.

16. The compound according to claim 15 which is [1α,3β,5Z,7E]-1,3-bis[(tetrahydro-2H-pyran-2-yl)oxy]-25-(1-ethoxyethoxy)-24,24-difluoro-9,10-secocholesta-5,7,10(19)-triene.

17. A compound of the formula

[Structure IV]

wherein F is fluorine and R, $R^1$ and $R^2$ are tri-lower alkylsilyl, di-lower alkylarylsilyl, lower alkyldiarylsilyl or triarylsilyl or a group of the formula $$R^5-O-\underset{\underset{R^4}{|}}{\overset{\overset{R^3}{|}}{C}}- \quad \text{III}$$

wherein $R^3$ is hydrogen or lower alkyl; $R^4$ and $R^5$ each independently, are lower alkyl and $R^4$ and $R^5$ taken together are lower alkylene of from 3 to 6 carbon atoms.

18. The compound according to claim 17 wherein R, $R^1$ and $R^2$ are a group of the formula $$R^5-O-\underset{\underset{R^4}{|}}{\overset{\overset{R^3}{|}}{C}}- \quad \text{III}$$

wherein $R^3$ is hydrogen or lower alkyl; $R^4$ and $R^5$ each independently are lower alkyl and $R^4$ and $R^5$ taken together are lower aslkylene of from 3 to 6 carbon atoms.

19. The compound according to claim 18 which is [1α,3β]-1,3-bis-[(tetrahydro-2H-pyran-2-yl)oxy]-25-(1-ethoxyethoxy)-24,24-difluorocholest-5-ene.

20. A compound of the formula

[Structure VIII]

wherein F is fluorine, R,$R^1$ and $R^2$ are lower alkyl, aralkyl, aryl, tri-lower alkylsilyl, di-lower alkylarylsilyl, lower-alkyldiarylsilyl, triarylsilyl or a group of the formula $$R^5-O-\underset{\underset{R^4}{|}}{\overset{\overset{R^3}{|}}{C}}- \quad \text{III}$$

wherein $R^3$ is hydrogen or lower alkyl; $R^4$ and $R^5$ each independently is lower alkyl and $R^4$ and $R^5$ taken together are lower alkylene of from 3 to 6 carbon atoms and $R^6$ is lower alkyl, aralkyl, or aryl.

21. The compound according to claim 20 wherein R and $R^1$ are aralkyl, or tri-lower alkylsilyl, or R, $R^1$, and $R^2$ are a group of the formula

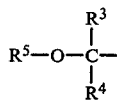   III wherein $R^3$ is hydrogen or lower alkyl; $R^4$ and $R^5$ each independently is lower alkyl and $R^4$ and $R^5$ taken together are lower alkylene of from 3 to 6 carbon atoms and $R^6$ is lower alkyl, aralkyl or aryl.

22. The compound according to claim 21 which is [1α,3β]-1,3-bis-[(tetrahydro-2H-pyran-2-yl)oxy]-25-(1-ethoxyethoxy)-24,24-difluorocholest-5-en-21-oic acid ethyl ester.

23. A compound of the formula

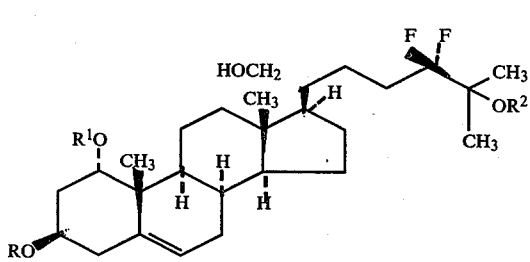   IX wherein F is fluorine and R, $R^1$, and $R^2$ are lower alkyl, aralkyl, aryl, tri-lower alkylsilyl, di-lower alkylarylsilyl, lower-alkyldiarylsilyl, triarylsilyl or a group of the formula

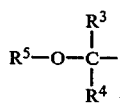   III wherein $R^3$ is hydrogen or lower alkyl; $R^4$ and $R^5$ each independently is lower alkyl and $R^4$ and $R^5$ taken together are lower alkylene of from 3 to 6 carbon atoms.

24. The compound according to claim 23 wherein R, and $R^1$ are aralkyl or tri-lower alkylsilyl or R, $R^1$ and $R^2$ are a group of the formula

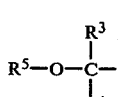   III wherein $R^3$ is hydrogen or lower alkyl; $R^4$ and $R^5$ each independently is lower alkyl and $R^4$ and $R^5$ taken together are lower alkylene of from 3 to 6 carbon atoms.

25. The compound according to claim 24 which is [1α,3β]-1,3-bis[(tetrahydro-2H-pyran-2-yl)oxy]-25-(1-ethoxyethoxy)-24,24-difluorocholest-5-en-21-ol.

26. A compound of the formula

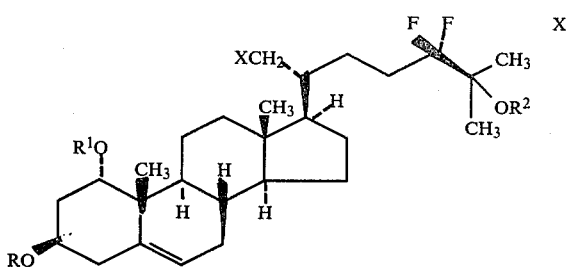   X wherein F is fluorine, X is iodo, bromo, chloro, lower alkylsulphonyloxy, phenylsulfonyloxy or substituted phenylsulfonyloxy, R, $R^1$ and $R^2$ are lower alkyl, aralkyl, aryl, tri-lower alkylsilyl, di-lower alkylarylsilyl, lower-alkyldiarylsilyl, triarylsilyl or group of the formula

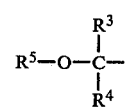   III wherein $R^3$ is hydrogen or lower alkyl; $R^4$ and $R^5$ each independently is lower alkyl and $R^4$ and $R^5$ taken together are lower alkylene of from 3 to 6 carbon atoms.

27. The compound according to claim 26 wherein X is phenylsulfonyloxy, substituted phenylsulfonyloxy, or iodo, R and $R^1$ are aralkyl, or tri-lower alkylsilyl or R, $R^1$ and $R^2$ are a group of the formula

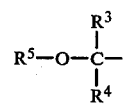   III wherein $R^3$ is hydrogen or lower alkyl; $R^4$ and $R^5$ each independently is lower alkyl and $R^4$ and $R^5$ taken together are lower alkylene of from 3 to 6 carbon atoms.

28. The compound according to claim 27 which is [1α,3β]-1,3-bis-[(tetrahydro-2H-pyran-2-yl)oxy]-25-(1-ethoxyethoxy)-24,24-difluoro-21-iodo-cholest-5-ene.

29. The compound according to claim 27 which is [1α,3β]-1,3-bis[(tetrahydro-2H-pyran-2-yl)oxy]-25-(1-ethoxyethoxy)-24,24-difluorocholest-5-en-21-ol 21-(4-methylbenzenesulfonate).

30. A compound of the formula

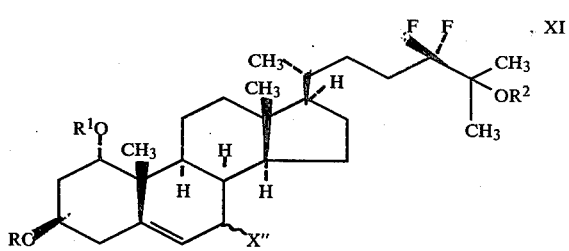   XI wherein F is fluorine, X" is iodo, bromo, chloro or R, $R^1$ and $R^2$ are tri-lower alkylsilyl, di-lower alkylarylsilyl, lower-alkyldiarylsilyl, triarylsilyl or a group of the formula

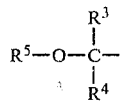

wherein $R^3$ is hydrogen or lower alkyl; $R^4$ and $R^5$ each independently is lower alkyl and $R^4$ and $R^5$ taken together are lower alkylene of from 3 to 6 carbon atoms.

31. The compound according to claim 30 wherein R, $R^1$ and $R^2$ are a group of the formula

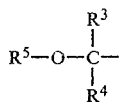

wherein $R^3$ is hydrogen or lower alkyl; $R^4$ and $R^5$ each independently is lower alkyl and $R^4$ and $R^5$ taken together are lower alkylene of from 3 to 6 carbon atoms.

32. A compound of the formula

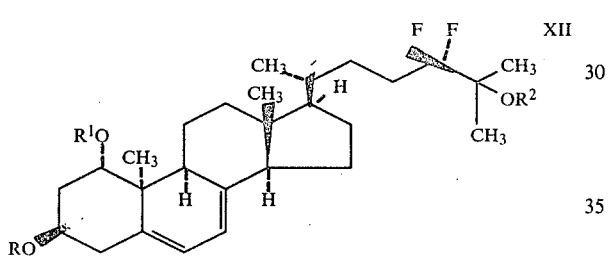

wherein F is fluorine and R, $R^1$, and $R^2$ are tri-lower alkylsilyl, di-lower alkylarylsilyl, lower-alkyldiarylsilyl, triarylsilyl or a group of the formula

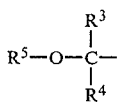

wherein $R^3$ is hydrogen or lower alkyl; $R^4$ and $R^5$ each independently is lower alkyl and $R^4$ and $R^5$ taken together are lower alkylene of from 3 to 6 carbon atoms.

33. The compound according to claim 32 wherein R, $R^1$ and $R^2$ are a group of the formula

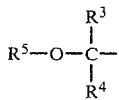

wherein $R^3$ is hydrogen or lower alkyl; $R^4$ and $R^5$ each independently is lower alkyl and $R^4$ and $R^5$ taken together are lower alkylene of from 3 to 6 carbon atoms.

34. A compound of the formula

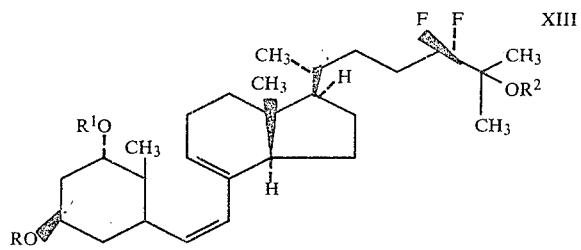

wherein F is fluorine and R, $R^1$ and $R^2$ are tri-lower alkylsilyl, di-lower alkylarylsilyl, lower-alkyldiarylsilyl, triarylsilyl or a group of the formula

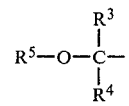

wherein $R^3$ is hydrogen or lower alkyl; $R^4$ and $R^5$ each independently is lower alkyl and $R^4$ and $R^5$ taken together are lower alkylene of from 3 to 6 carbon atoms.

35. The compound according to claim 25 wherein R, $R^1$ and $R^2$ are a group of the formula

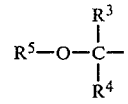

wherein $R^3$ is hydrogen or lower alkyl; $R^4$ and $R^5$ each independently is lower alkyl and $R^4$ and $R^5$ taken together are lower alkylene of from 3 to 6 carbon atoms.

36. A compound of the formula

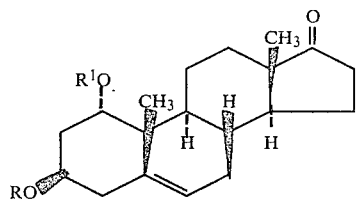

wherein R and $R^1$, are lower alkyl, aralkyl, aryl, tri-lower alkylsilyl, di-lower alkylarylsilyl, lower-alkyldiarylsilyl, triarylsilyl or R and $R^1$ are a group of the formula

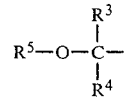

wherein $R^3$ is hydrogen or lower alkyl; $R^4$ and $R^5$ each independently is lower alkyl and $R^4$ and $R^5$ taken together are lower alkylene of from 3 to 6 carbon atoms.

37. The compound according to claim 36 wherein R, and $R^1$ are aralkyl, tri-lower alkylsilyl or R and $R^1$ are a group of the formula

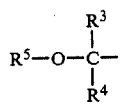 III wherein $R^3$ is hydrogen or lower alkyl; $R^4$ and $R^5$ each independently is lower alkyl and $R^4$ and $R^5$ taken together are lower alkylene of from 3 to 6 carbon atoms.

38. The compound according to claim 37 which is [$\alpha,3\beta$]-1,3-bis[(tetrahydro-2H-pyran-2-yl)oxy]androst-en-17-one.

39. A compound of the formula

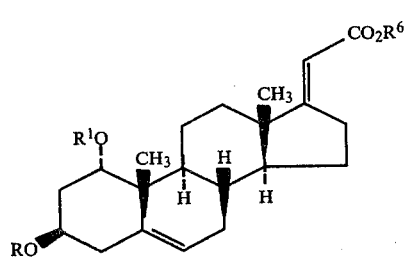 V-C wherein R and $R^1$, are lower alkyl, aralkyl, aryl, tri-lowr alkylsilyl, di-lower alkylarylsilyl, loweralkyldiarylsilyl, triarylsilyl or a group of the formula

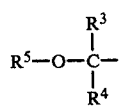 III wherein $R^3$ is hydrogen or lower alkyl; $R^4$ and $R^5$ each independently is lower alkyl and $R^4$ and $R^5$ taken together are lower alkylene of from 3 to 6 carbon atoms and $R^6$ is lower alkyl, aralkyl or aryl.

40. The compound according to claim 39 wherein R, and $R^1$ are aralkyl or tri-lower alkylsilyl or R and $R^1$ are a group of the formula

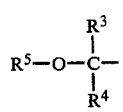 III wherein $R^3$ is hydrogen or lower alkyl; $R^4$ and $R^5$ each independently is lower alkyl and $R^4$ and $R^5$ taken together are lower alkylene of from 3 to 6 carbon atoms and $R^6$ is lower alkyl, aralkyl, or aryl.

41. The compound according to claim 40 which is [$1\alpha,3\beta,17(20)E$]-1,3-bis-[(tetra-2H-pyran-2-yl)oxy]-pregn-5,17(20)-dien-21-oic acid ethyl ester.

42. A compound of the formula

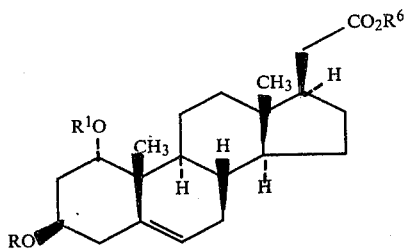 V wherein R and $R^1$, are lower alkyl, aralkyl, aryl, tri-lower alkylsilyl, di-lower alkylarylsilyl, loweralkyldiarylsilyl, triarylsilyl or a group of the formula

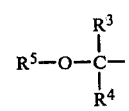 III wherein $R^3$ is hydrogen or lower alkyl; $R^4$ and $R^5$ each independently is lower alkyl and $R^4$ and $R^5$ taken together are lower alkylene of from 3 to 6 carbon atoms and $R^6$ is lower alkyl, aralkyl or aryl.

43. The compound according to claim 42 wherein R, and $R^1$ are aralkyl or tri-lower alkylsilyl or R and $R^1$ are a group of the formula

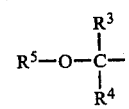 III wherein $R^3$ is hydrogen or lower alkyl; $R^4$ and $R^5$ each independently is lower alkyl and $R^4$ and $R^5$ taken together are lower alkylene of from 3 to 6 carbon atoms and $R^6$ is lower alkyl, aralkyl, or aryl.

44. The compound according to claim 43 which is [$1\alpha,3\beta$]-1,3-bis[(tetrahydro-2H-pyran-2-yl)oxy]-pregn-5-en-21-oic acid ethyl ester.

45. A compound of the formula

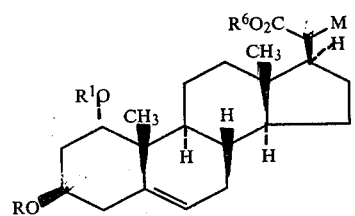 VI wherein R and $R^1$ are lower alkyl, aralkyl, aryl, trilower alkylsilyl, di-lower alkylarylsilyl, loweralkyldiarylsilyl, triarylsilyl or a group of the formula

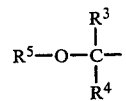 III wherein $R^3$ is hydrogen or lower alkyl; $R^4$ and $R^5$ each independently is lower alkyl and $R^4$ and $R^5$ taken together are lower alkylene of from 3 to 6 carbon atoms, $R^6$ is lower alkyl, aralkyl or aryl, and M is lithium, sodium, potassium, magnesium/2 or zinc/2.

46. The compound according to claim 45 wherein R, and R¹ are aralkyl or tri-lower alkylsilyl or R and R¹ are a group of the formula

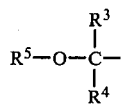

wherein $R^3$ is hydrogen or lower alkyl; $R^4$ and $R^5$ each independently is lower alkyl and $R^4$ and $R^5$ taken together are lower alkylene of from 3 to 6 carbon atoms, $R^6$ is lower alkyl, aralkyl, or aryl and M is lithium, sodium, potassium, magnesium/2 or zinc/2.

47. The compound according to claim 46, the lithium enolate of [1α,3β]-1,3-bis[(tetrahydro-2H-pyranyl-2-yl)oxy]pregn-5-en-21-oic acid ethyl ester.

* * * * *